US012667390B2

(12) United States Patent
Samchukov et al.

(10) Patent No.: US 12,667,390 B2
(45) Date of Patent: Jun. 30, 2026

(54) ORTHOPEDIC SPRING HINGE SYSTEMS AND METHODS

(71) Applicants:Orthofix S.R.L., Bussolengo (IT); Texas Scottish Rite Hospital for Children, Dallas, TX (US)

(72) Inventors: Mikhail L. Samchukov, Coppell, TX (US); Karen D. Standefer, Flower Mound, TX (US); John D. Ross, Ovilla, TX (US); Alexander M Cherkashin, Flower Mound, TX (US); Daniele Venturini, Povegliano Veronese (IT); Andrea Ottoboni, Giacciano con Baruchella (IT); Michael Lupatini, San Martino della Battaglia (IT)

(73) Assignees: Texas Scottish Rite Hospital for Children, Dallas, TX (US); Orthofix S.R.L., Verona (IT)

( * ) Notice: Subject to any disclaimer, the term of this patent is extended or adjusted under 35 U.S.C. 154(b) by 722 days.

(21) Appl. No.: 17/962,158

(22) Filed: Oct. 7, 2022

(65) Prior Publication Data

US 2023/0075823 A1 Mar. 9, 2023

Related U.S. Application Data

(63) Continuation of application No. 17/470,116, filed on Sep. 9, 2021, now Pat. No. 11,497,527.

(51) Int. Cl.
*A61B 17/62* (2006.01)
*A61B 17/66* (2006.01)
*A61B 17/60* (2006.01)

(52) U.S. Cl.
CPC .............. *A61B 17/62* (2013.01); *A61B 17/66* (2013.01); *A61B 2017/606* (2013.01)

(58) Field of Classification Search
CPC ......... A61B 17/60; A61B 17/62; A61B 17/64; A61B 17/6425; A61B 17/645;
(Continued)

(56) References Cited

U.S. PATENT DOCUMENTS 3,877,424 A * 4/1975 Murray .................. A61B 17/60
606/92
3,977,397 A 8/1976 Kalnberz et al.
(Continued)

OTHER PUBLICATIONS

European Patent Office, "Partial European Search Report", for Application No. ep 21195761, Feb. 10, 2022.
(Continued)

*Primary Examiner* — Eduardo C Robert
*Assistant Examiner* — Michelle C Green
(74) *Attorney, Agent, or Firm* — Haynes and Boone, LLP

(57) ABSTRACT

An orthopedic spring hinge and associated external fixation systems for the treatment of anatomical joint dysfunctions, and more particularly, to a spring hinge comprising a first base member, a second base member, a flexible first spring having a first longitudinal axis extending from the first base member to the second base member, and a flexible second spring spaced apart from the first spring and having a second longitudinal axis extending from the first base member to the second base member. The spring hinge is configured to have a maximum bending resistance in a first plane extending between the first spring and the second spring and a minimum bending resistance in a second plane orthogonal to the first plane.

22 Claims, 21 Drawing Sheets

(58) Field of Classification Search
CPC . A61B 17/6433; A61B 17/6491; A61B 17/66; B61B 17/7023
See application file for complete search history.

(56) References Cited

U.S. PATENT DOCUMENTS

| | | | |
|---|---|---|---|
| 5,681,309 A | | 10/1997 | Ross, Jr. et al. |
| 6,030,386 A | | 2/2000 | Taylor et al. |
| 6,162,223 A | * | 12/2000 | Orsak ................ A61B 17/6425 606/59 |
| 6,540,708 B1 | | 4/2003 | Manspeizer |
| 8,425,568 B2 | | 4/2013 | Bhatnagar et al. |
| 9,206,871 B2 | | 12/2015 | Phillips |
| 9,808,290 B2 | * | 11/2017 | Landry .............. A61B 17/6425 |
| 10,413,328 B1 | | 9/2019 | Klein, Jr. et al. |
| 10,945,763 B2 | | 3/2021 | Samchukov et al. |
| 2004/0249375 A1 | * | 12/2004 | Agee .................. A61B 17/6425 606/54 |
| 2005/0056979 A1 | | 3/2005 | Studer et al. |
| 2005/0127729 A1 | | 6/2005 | Knoblock et al. |
| 2005/0261680 A1 | * | 11/2005 | Draper .............. A61B 17/6425 606/59 |
| 2007/0049930 A1 | | 3/2007 | Hearn et al. |
| 2007/0049936 A1 | * | 3/2007 | Colleran ............ A61B 17/7011 606/70 |
| 2007/0233091 A1 | * | 10/2007 | Naifeh ............... A61B 17/7005 606/279 |
| 2008/0275557 A1 | * | 11/2008 | Makower ............... A61B 17/68 623/18.11 |
| 2008/0275563 A1 | | 11/2008 | Makower et al. |
| 2010/0320660 A1 | | 12/2010 | Takeda et al. |
| 2011/0208187 A1 | | 8/2011 | Wong |
| 2013/0013066 A1 | | 1/2013 | Landry et al. |
| 2014/0336648 A1 | | 11/2014 | Van Aaken et al. |
| 2016/0015428 A1 | | 1/2016 | Bowden et al. |
| 2018/0250139 A1 | | 9/2018 | Luboshitz et al. |
| 2019/0110816 A1 | | 4/2019 | Ross et al. |
| 2019/0365420 A1 | | 12/2019 | Samchukov et al. |

OTHER PUBLICATIONS

Chaudhury, A et al. "Analysis of prismatic springs of non-circular coil shape and non-prismatic 21 springs of cirucular coil shape by analytical and finite element methods." Journal of Computational Design and Manufacturing. Feb. 8, 2017; pp. 178-191.

* cited by examiner

ORTHOPEDIC SPRING HINGE SYSTEMS AND METHODS

CROSS-REFERENCE TO RELATED APPLICATIONS

This application is a continuation of U.S. patent application Ser. No. 17/470,116 filed Sep. 9, 2021, entitled, "ORTHOPEDIC SPRING HINGE SYSTEMS AND METHODS", which is incorporated herein by reference in its entirety.

TECHNICAL FIELD

This disclosure is generally directed to orthopedic spring hinges and associated external fixation systems.

BACKGROUND

External fixation systems are used in a variety of surgical procedures including limb lengthening, deformity correction, fracture reduction, and treatment of non-unions, malunions, and bone defects. A rigid framework comprising external fixators, which may be referred to as "supports" herein, (e.g., rings, half rings, ⅝ rings, etc.) is placed externally around an affected limb and attached to bone segments using wires, pins, or other fixation elements. The external supports of the rigid framework are interconnected by rods directly or in conjunction with uni-planar or multi-planar hinges, which allow a user to connect external fixators that are not parallel to each other at the time of application or to permit manipulation of anatomical joints within the region encompassed by the external fixation system.

For treatment of various pathologies, it is beneficial to allow for controlled movement about a hinge that is disposed between two external supports. Introducing controlled movement can accelerate bone healing and improve mobility of joints. For example, it may be beneficial to secure one or more hinges between two external supports to allow for limited pivotal movement of an anatomical joint. A hinge may allow for pivotal rotation of an anatomical joint such that movement may be reintroduced to a patient's joint. Such hinges, however, should provide for sufficient stability and reduce movement along axes other than those of the respective anatomical joint(s). Excessive movement along other axes may negatively impact the healing process and otherwise cause damage or pain to a patient. For example, translational movement (or "shearing") of a hinge during joint movement may harm the anatomical joint structure and impair restoration of its function.

Traditional mono-axial mechanical hinges have been used in orthopedic treatment but have significant limitations. They may not adequately conform to the anatomical axis of a joint, particularly if the joint axis changes dynamically. When a joint rotates or moves, the corresponding axis of rotation may shift in one or more directions. Furthermore, some anatomical joints are complex, such as the ankle and wrist, and are not constrained to a static axis of rotation. If an external fixation system has an axis of rotation that is out of alignment with the anatomical axis of rotation, pivoting of the joint could result in pain, discomfort, subluxation or dislocation of the joint, and/or damage to the joint or adjacent tissue.

A traditional coil spring may be used in hinges to allow for the axis of rotation to shift or adjust to the position of the anatomical axis of rotation of a particular joint during movement. However, many coil springs have inherent instability and fail to limit movement to one or more desired planes. When a coil spring bends in a particular direction, the internal layers that make up the spring are susceptible to shearing forces which can result in a shearing movement. Accordingly, traditional coil springs may fail to provide sufficient stability when used in external fixation systems.

Accordingly, there is a need for improved spring hinges that provide sufficient stability and limit pivotal movement of a joint to a finite number of planes or directions while also dynamically adapting to a shifting anatomical axis of rotation.

SUMMARY

The present disclosure relates in general to orthopedic hinges suitable for use with external fixators and as part of external fixation systems. In some embodiments, orthopedic hinges of the present disclosure may provide for pivotal movement about an axis of an anatomical joint while reducing or completely preventing unwanted pivotal movement about one or more other axes of the anatomical joint and unwanted translational or shearing movement of said anatomical joint.

In some embodiments, an orthopedic spring hinge includes a first base member, a second base member, a flexible first spring having a first longitudinal axis extending from the first base member to the second base member, and a flexible second spring spaced apart from the first spring and having a second longitudinal axis extending from the first base member to the second base member. The spring hinge may be configured to have a maximum bending resistance to rotation in a first plane extending between the first spring and the second spring and a minimum bending resistance to rotation in a second plane orthogonal to the first plane and parallel to the first longitudinal axis. In other words, the spring hinge may facilitate pivotal movement of an anatomical joint in a desired direction while restricting or resisting pivotal movement of the anatomical joint in undesired directions.

In some embodiments of an orthopedic spring hinge, the first spring and/or the second spring hinge may be formed from a coil spring having a helical structure with a central cavity. A coil spring may be formed of a plurality of spirals layered against one another when the coil spring is in an unexpanded state. This structure may maintain a desired gap between contacting surfaces of the anatomical joint while permitting joint motion and preserving that gap during movement by maintaining the coil spring in compression to push external fixators of the external fixation system apart.

In some embodiments, a coil spring of each of the first and second springs may have a width of about 5 to 25 mm and/or a length of about 15 to 50 mm.

In some embodiments, a base member may include a first spring connection bore and a second spring connection bore, each of the first and second spring connection bores configured to receive an end of a respective spring. A spring connection bore may be internally threaded to engage an external surface of a spring.

In some embodiments, an orthopedic spring hinge may include at least one dowel. For example, an orthopedic spring hinge may include one dowel for each spring connection bore. A dowel may be externally threaded to engage an internal surface of a spring to secure the spring to a base member. A dowel may be generally cylindrical or may be tapered such that the dowel exerts a force on the spring into which it is inserted which increases as the dowel is threaded into the spring as the width of the portion of the dowel engaging the spring increases. In this regard, a spring may be secured between an external surface of a dowel and an internal surface of a spring connection bore in a base member.

In some embodiments, an orthopedic spring hinge may include at least one adjustment bolt extendable into a spring, such as a coil spring, a selectable distance to rigidize a first portion of the spring hinge while allowing a second portion of the spring hinge to bend. Adjusting the selectable distance, for example by threading the adjustment bolt further into the spring or further out of the spring, may alter a bending resistance of the spring hinge by altering a length of a portion of the spring hinge which is able to bend. An adjustment bolt may be threaded through a bore in a dowel, threaded into coils of the spring, or secured to the spring hinge in any other suitable manner which permits the adjustment bolt to extend into the spring by a selectable distance.

In some embodiments, a base member may include a bolt connection bore configured to receive a bolt, or any other suitable device, to secure the base member to an external fixation system comprising a plurality of external fixators. A base member may be configured to be secured to an external fixation system such that the second plane, in which the spring hinge has a minimum or reduced bending resistance, is parallel to a plane in which an anatomical joint encompassed by the external fixation system rotates. A spring hinge may be configured such that an axis of rotation of the spring hinge as the spring hinge bends in the second plane translates dynamically in conjunction with translation of an anatomical axis of rotation of the anatomical joint. In this regard, embodiments of a spring hinge according to the present disclosure may provide unconstrained or constrained movement of an anatomical joint without a predetermined or defined axis of rotation. This may allow the joint to move about its anatomical axis of rotation. Orientation of two springs in the same plane (e.g., coronal plane), which is orthogonal to joint plane of movement (e.g., sagittal plane movement of the ankle joint) significantly improves shear stability of the joint (e.g., in the coronal plane) while allowing joint flexion/extension in the joint plane of movement (e.g., in the sagittal plane) and some, although restricted in some embodiments, torsion.

In some embodiments, at least one of the first and second springs may comprise a flexible blade having a thickness in a direction parallel to the second plane that is less than a width of the flexible blade in a direction parallel to the first plane. In some embodiments, at least one of the first and second springs may comprise a slotted spring having a plurality of slots extending into a spring body in a direction transverse to the longitudinal axis of the spring. In some embodiments, at least one of the first and second springs may comprise a ribbon spring.

In some embodiments, at least one of the first and second springs may comprise a coil spring and a secondary spring extending within a central cavity of the coil spring. A secondary spring may comprise a coil spring, a flexible blade, a slotted spring, a ribbon spring, an elastic structure (e.g., a plastic rod with or without a molded fabric), or any other suitable spring device.

In some embodiments, an orthopedic spring hinge may include a locking structure configured to rigidly secure the spring hinge to prevent rotation of the first base member with respect to the second base member. A locking structure may include a first locking plate and a second locking plate configured to receive the first spring and the second spring therebetween when the first locking plate is secured to the second locking plate. A locking structure may include a rigid lock plate removably attachable, directly or indirectly, to the first base member and the second base member. A locking structure may include at least one tie rod configured to removably extend between the first base member and the second base member.

In some embodiments, each of the first spring and second spring may include at least one integrated connector configured to threadingly engage, directly or indirectly, the first base member or the second base member.

In some embodiments, an orthopedic spring hinge may include a first base member having a first longitudinal axis, a second base member having a second longitudinal axis parallel to the first longitudinal axis, a flexible first spring extending from the first base member to the second base member, and a flexible second spring extending from the first base member to the second base member. The second spring may be spaced apart from the first spring along the first and second longitudinal axes. A spring hinge may be configured to have a first bending resistance to rotation between the first base member and the second base member in a first plane parallel to the first and second longitudinal axes and to have a second bending resistance to rotation between the first base member and the second base member in a second plane transverse to the first and second longitudinal axes. The first bending resistance may be greater than the second bending resistance.

In some embodiments, an orthopedic spring hinge may include a first base member comprising a first arm extending on a first lateral side of the spring hinge, a second base member comprising a second arm extending on a second lateral side of the spring hinge opposite the first side, at least one flexible spring having a longitudinal axis extending from the first base member to the second base member, and a hinge connector extending from the first arm to the second arm. The hinge connector may be configured to pivot with respect to one or both of the first arm and the second arm.

In some embodiments, the hinge connector may be secured to the first arm with a first pin joint and may be secured to the second arm with a second pin joint. A spring hinge may be configured to prevent rotation of the first base member with respect to the second base member about an axis parallel to the longitudinal axis of the flexible spring. A spring hinge may be configured to prevent rotation of the first base member with respect to the second base member about a first axis transverse to the longitudinal axis of the flexible spring while permitting rotation of the first base member with respect to the second base member about a second axis transverse to the longitudinal axis of the flexible spring and the first axis.

In some embodiments, one or both of a first base member and a second base member may include a bolt connection bore configured to receive a bolt, or other suitable device, to secure the first and second base members to an external fixation system. In some embodiments, each of the first and second base members may further include at least one spring connection bore configured to receive an end of a flexible spring. A spring connection bore may be internally threaded to engage an external surface of the flexible spring.

In some embodiments, a spring hinge may include a first dowel that may be externally threaded to engage an internal surface of a first end portion of a flexible spring to secure the flexible spring to a base member and a second dowel that may be externally threaded to engage an internal surface of a second end portion of the same or a different flexible spring to secure the flexible spring to the same or a different base member. A dowel may be tapered to exert a force on the flexible spring which increases as the first dowel is threaded into the first end portion of the flexible spring.

In some embodiments, a first base member and a second base member may be configured to be secured to an external fixation system such that a longitudinal axis of the hinge connector is parallel to a plane in which an anatomical joint encompassed by the external fixation system rotates.

In some embodiment, a spring hinge may be configured such that an axis of rotation of the spring hinge as the flexible spring bends translates dynamically in conjunction with translation of an anatomical axis of rotation of the anatomical joint.

In some embodiments, a flexible spring may have at least one integrated connector configured to threadingly engage a base member.

In some embodiments, a hinge connector may be configured to resist shearing movement between a first base member and a second base member. In some embodiments, a second hinge connector may extend from a first arm to a second arm. A second hinge connector may be configured to pivot with respect to the first arm and the second arm. A first hinge connector may be disposed on one side of a first arm and a second arm that is opposite a side of the first arm and the second arm on which the second hinge connector is disposed. In some embodiments, a second hinge connector may extend from a third arm of a first base member to a fourth arm of a second base member. The second hinge connector may be configured to pivot with respect to the third arm and the fourth arm. A first hinge connector and a second hinge connector may be disposed on an internal side of the arms of one or more base members, such as between two arms of a first base member and between two arms of a second base member.

In some embodiments, a first base member may include a first arm and a third arm and a second base member may include a second arm and a fourth arm. A hinge connector may be secured to the first arm and the third arm at one end with a first pin and secured to the second arm and the fourth arm at the other end with a second pin.

In some embodiments, a spring hinge may include a second flexible spring having a longitudinal axis extending from a first base member to a second base member. A hinge connector may extend through a central region of a spring hinge such as between a first flexible spring and a second flexible spring to pass from one side of a plane extending between the first and second flexible springs to the other side of the plane. In some embodiments, a first arm of a first base member and a second arm of a second base member may each be bifurcated into two branches. A hinge connector may be secured between the two branches of a respective arm with a pin.

In some embodiments, one or both of a first flexible spring and a second flexible spring may comprise a coil spring or a blade spring.

In some embodiments, an orthopedic spring hinge may include a first base member, a second base member, and a flexible spring extending from the first base member to the second base member along a longitudinal axis. The flexible spring may have a length in a direction of the longitudinal axis, a width less than the length, and a thickness less than the width. A flexible spring may have a plurality of rigid hinge members each extending parallel to the width of the flexible hinge. The plurality of rigid hinge members may be partially or fully embedded in an elastomer or other resilient covering. The flexible spring may be configured to prevent bending of the spring hinge within a first plane in which the height and width of the flexible spring extend and to permit bending of the spring hinge within a second plane in which the height and thickness of the flexible spring extend.

In some embodiments, each of the plurality of rigid hinge members may have a recess configured to receive a portion of an adjacent one of the rigid hinge members. The recess may comprise a concave groove configured to receive a convex outer surface of the portion of the adjacent one of the rigid hinge members. In some embodiments, each of the plurality of rigid hinge members may have an elongated (or ridged) convex protrusion configured to nest in a corresponding concave slot of an adjacent one of the rigid hinge members. The nested arrangement of the plurality of rigid hinge members may prevent twisting of the flexible hinge.

In some embodiments, each of the first and second base members may include a bolt connection bore configured to receive a bolt to secure the first and second base members to an external fixation system comprising a plurality of external fixators. The first and second base members may be configured to be secured to an external fixation system such that the thickness of the flexible spring is oriented parallel to a plane in which an anatomical joint encompassed by the external fixation system rotates. A spring hinge may be configured such that an axis of rotation of the spring hinge as the flexible spring bends within the second plane translates dynamically in conjunction with translation of an anatomical axis of rotation of the anatomical joint.

In some embodiments, an orthopedic spring hinge may include a first base member having a first bolt connection bore for securing the spring hinge to an external fixation system, a second base member having a second bolt connection bore for securing the spring hinge to the external fixation system, and a flexible spring extending from the first base member to the second base member. A longitudinal axis of the flexible spring may be offset from a longitudinal axis of the first bolt connection bore and a longitudinal axis of the second bolt connection bore. The longitudinal axis of the first bolt connection bore and the longitudinal axis of the second bolt connection bore may or may not aligned along a common axis.

In some embodiments, a method for treating an anatomical joint dysfunction may include fixing a first portion and a second portion of a limb on opposite sides of an anatomical joint with a first external fixator and a second external fixator such that the first and second external fixators are positioned on either side of the anatomical joint. The method may further include connecting the first and second external fixators with one or more orthopedic spring hinges disposed therebetween. Such an orthopedic spring hinge may comprise any suitable spring hinge disclosed herein. For example, in some embodiments, a spring hinge may include a first base member comprising a first arm extending on a first lateral side of the spring hinge, a second base member comprising a second arm extending on a second lateral side of the spring hinge opposite the first side, a flexible spring having a longitudinal axis extending from the first base member to the second base member, and a hinge connector extending from the first arm to the second arm. The hinge connector may be configured to pivot with respect to the first arm and the second arm. The spring hinge may be aligned relative to the anatomical joint to permit rotation of the anatomical joint within a first plane parallel to a longitudinal axis of the hinge connector and to restrict one or both of translation and rotation of the anatomical joint within planes orthogonal to the first plane.

In some embodiments, a spring hinge may be self-aligning. At least one spring hinge may be positioned between external fixators of an external fixation system. For example, two spring hinges may be disposed on opposite sides of an external fixation frame (e.g., medial and lateral sides) loosely (e.g., without tightening the mounting bolts/nuts at the mounting holes of the external fixators) and then bent by joint motion or by imitating joint motion. Because a spring hinge having a plurality of springs aligned along a plane will have a reduced bending resistance (e.g., rigidity) in one direction as opposed to an orthogonal direction, during the flexion/extension motion the spring hinges will rotate until they are aligned in the same plane (e.g., coronal plane) which may correspond to a desired plane of movement of the joint. Once aligned, the spring hinges may be locked in this orientation by tightening the bolts, nuts, or other securing mechanism at the mounting holes.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following. One or more features of any embodiment or aspect may be combinable with one or more features of other embodiment or aspect.

BRIEF DESCRIPTION OF THE DRAWINGS

The accompanying drawings illustrate implementations of the systems, devices, and methods disclosed herein and together with the description, serve to explain the principles of the present disclosure.

Figure 1:
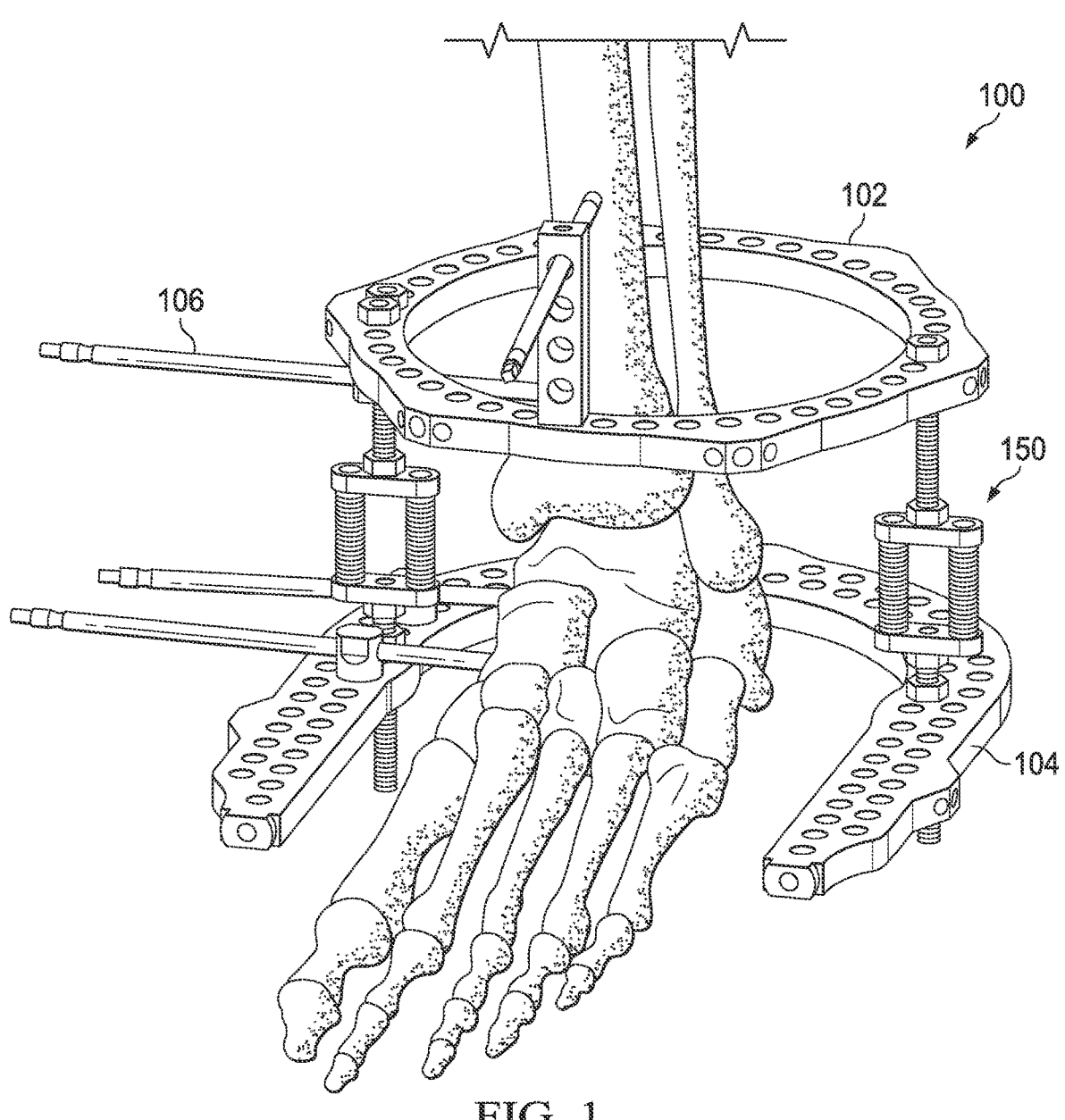
FIG. 1 is a perspective view of an external fixation system in accordance with the present disclosure.

These Figures will be better understood by reference to the following Detailed Description.

DETAILED DESCRIPTION

For the purpose of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or Figures, when those same elements or features appear in subsequent Figures, without such a high level of detail. It is fully contemplated that the features, components, and/or steps described with respect to one or more implementations or Figures may be combined with the features, components, and/or steps described with respect to other implementations or Figures of the present disclosure. For simplicity, in some instances the same or similar reference numbers are used throughout the drawings to refer to the same or like parts.

The present disclosure relates, in some embodiments, to orthopedic spring hinges suitable for use with external fixation devices. Orthopedic hinges of the present disclosure may be suitable for treatment of various anatomical joints including, but not limited to, the wrist, elbow, knee, or ankle.

FIG. 1 depicts an example external fixation system in accordance with the present disclosure. As depicted, an external fixation system 100 includes a plurality of external fixators including external fixation ring 102 and external fixator 104 which, in the illustrated embodiment, is a U-shaped external fixator. A plurality of rods 106 extend from fixtures secured to the external fixators and into bone, thereby securing the external fixation system 100 to the patient. One or more spring hinges 150 may be secured between external fixators to permit, yet control, movement of one external fixator with respect to another. It should be appreciated that any number of rods, fixtures, spring hinges, and external fixators of any suitable shape(s) and type(s) may be used in the construction of an external fixation system.

Spring hinges of the present disclosure may comprise certain features that advantageously allow for pivotal movement about an anatomical joint while reducing or completely preventing unwanted translational or shearing movement across said anatomical joint. Further, embodiments of the present disclosure may limit the pivotal movement of an anatomical joint to a finite number of planes or directions, while also being able to dynamically adapt to the shifting anatomical axis of rotation during movement of a corresponding anatomical joint. For example, with regard to the illustrated example of FIG. 1, the external fixation system 100 may limit the pivotal movement of the ankle joint to allow flexion and extension within the sagittal plane while preventing or limiting undesirable movement such as supination, pronation, and/or shear.

Figures 2A, 2B:
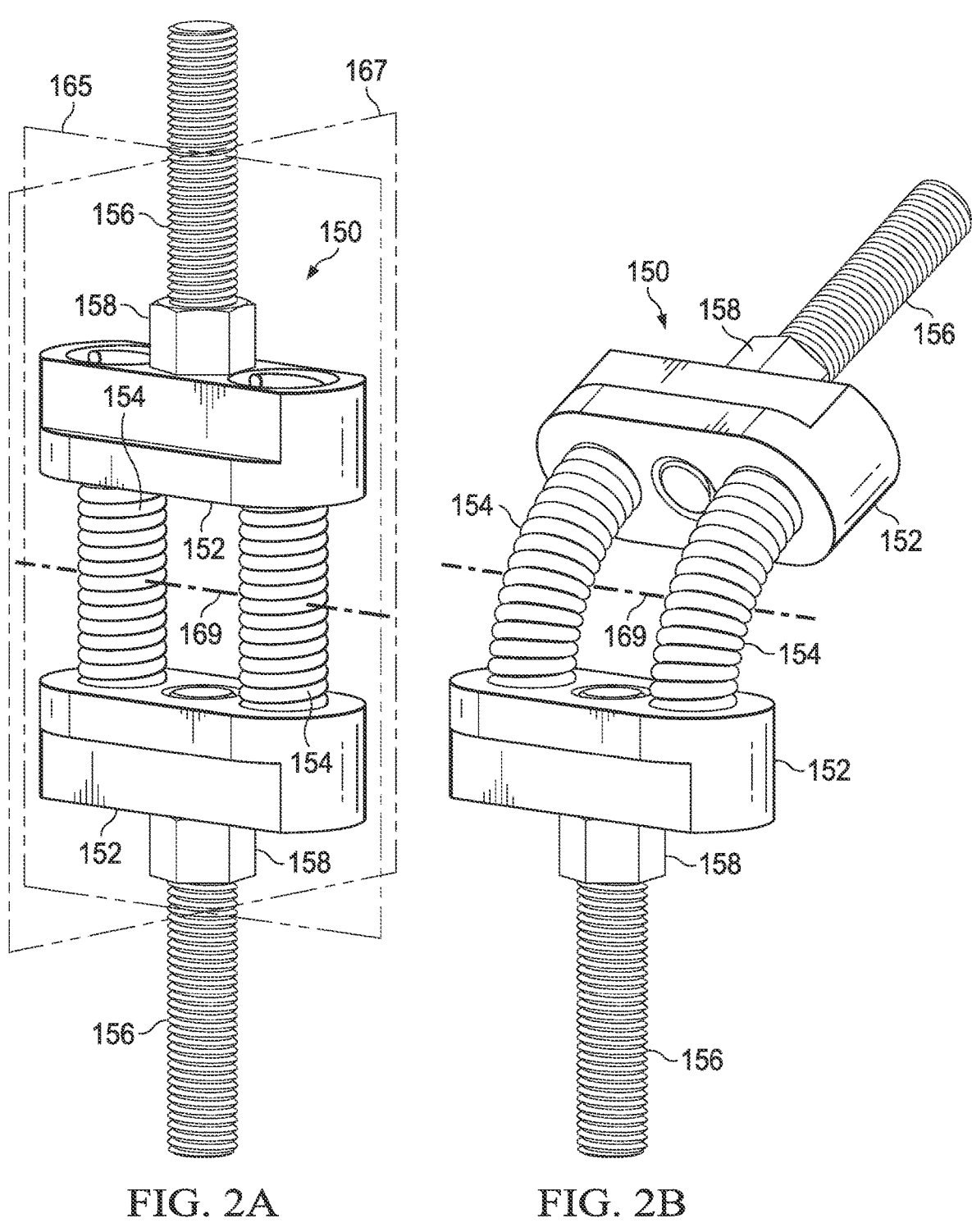
FIGS. 2A and 2B illustrate a perspective view of a spring hinge in an unexpanded and a flexed configuration, respectively, in accordance with the present disclosure.

FIGS. 2A and 2B illustrate spring hinge 150 which comprises two coil springs 154 extending between an upper base member and a lower base member 152. A bolt 156 may be attached to each base member 152 for securing the spring hinge 150 to an external fixation system as shown in FIG. 1. A nut 158 may be used to secure the bolt 156 to the base member 152. Although illustrated with two coil springs 154, it should be appreciated that any number of coil springs 154 may be used in spring hinge 150 within the scope of this disclosure.

Each coil spring 154 may be formed of a plurality of spirals that are layered or stacked upon one another. When a coil spring is in an unexpanded state the layers of spirals may rest upon one another as shown in FIG. 2A. When in a flexed or bent state, one side of the layers of spirals may rest upon one another and the layers of spirals on the opposing side may be spaced apart as shown in FIG. 2B.

Utilizing two coil springs 154 helps limit bending of the spring hinge 150 to a forward/rearward direction within plane 167 in which both coil springs 154 bend as shown in FIG. 2B while resisting lateral bending within plane 165.

Specifically, lateral bending of spring hinge 150 is resisted at least in part because one coil spring must be expanded while the other remains unexpanded and in compression. Accordingly, a bending resistance of the spring hinge 150 in a first direction (e.g., within second plane 167) is lower than a bending resistance of the spring hinge 150 in a second direction orthogonal to the first direction (e.g., within first plane 165). In this regard, the spring hinge 150 may be oriented within an external fixation system such that pivotal movement of the spring hinge, and in turn the anatomy of the patient, is substantially limited to axis of rotation 169 which may translate up/down and/or forward/backward during pivoting of the spring. Because anatomical axes do not always align with a fixed axis, the up/down and/or forward/backward translation during pivoting may better accommodate the anatomical axes than fixed axis systems. By arranging spring hinge 150 as shown in the example of FIG. 1, such that the coil springs 154 base members 152 are aligned within a frontal or coronal plane of the patient, pivotal movement of the ankle may be restricted to movement within the sagittal plane.

Coil springs 154 may be formed from any suitable materials including, but not limited to, stainless steel or tempered steel, and may be plated and/or coated with a plastic, polymer, and/or other resilient materials. Non-limiting examples of materials for use in forming coil springs and/or other external fixation system components discussed herein (such as spring hinge base members, external fixators, rods, bolts, nuts, etc.) include stainless steel, such as 304V, 304L, and 316LV stainless steel; mild steel; nickel-titanium alloy such as linear-elastic and/or super-elastic nitinol; other nickel alloys such as nickel-chromium-molybdenum alloys, nickel-copper alloys, nickel-cobalt-chromium-molybdenum alloys, nickel-molybdenum alloys, nickel-chromium alloys, nickel-molybdenum alloys, nickel-cobalt alloys, nickel-iron alloys, nickel-copper alloys, nickel-tungsten or tungsten alloys, and the like; cobalt-chromium alloys; cobalt-chromium-molybdenum alloys; platinum enriched stainless steel; titanium; aluminum, combinations thereof; and the like; reinforced (fabric) or non-reinforced plastics; or any other suitable materials with sufficient mechanical properties to limit and/or control movement of a joint during an orthopedic treatment.

Non-limiting examples of polymers for use in forming coil springs include polytetrafluoroethylene (PTFE), ethylene tetrafluoroethylene (ETFE), fluorinated ethylene propylene (FEP), polyoxymethylene (POM), polyether block ester, polyurethane (for example, Polyurethane 85A), polypropylene (PP), polyvinylchloride (PVC), polyether-ester, ether or ester based copolymers (for example, butylene/poly(alkylene ether) phthalate and/or other polyester elastomers), polyamide, elastomeric polyamides, block polyamide/ethers, polyether block amide (PEBA), ethylene vinyl acetate copolymers (EVA), silicones, polyethylene (PE), Marlex high-density polyethylene, Marlex low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12, perfluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbonates, ionomers, biocompatible polymers, other suitable materials, or mixtures, combinations, copolymers thereof, polymer/metal composites, and the like.

Figure 3:
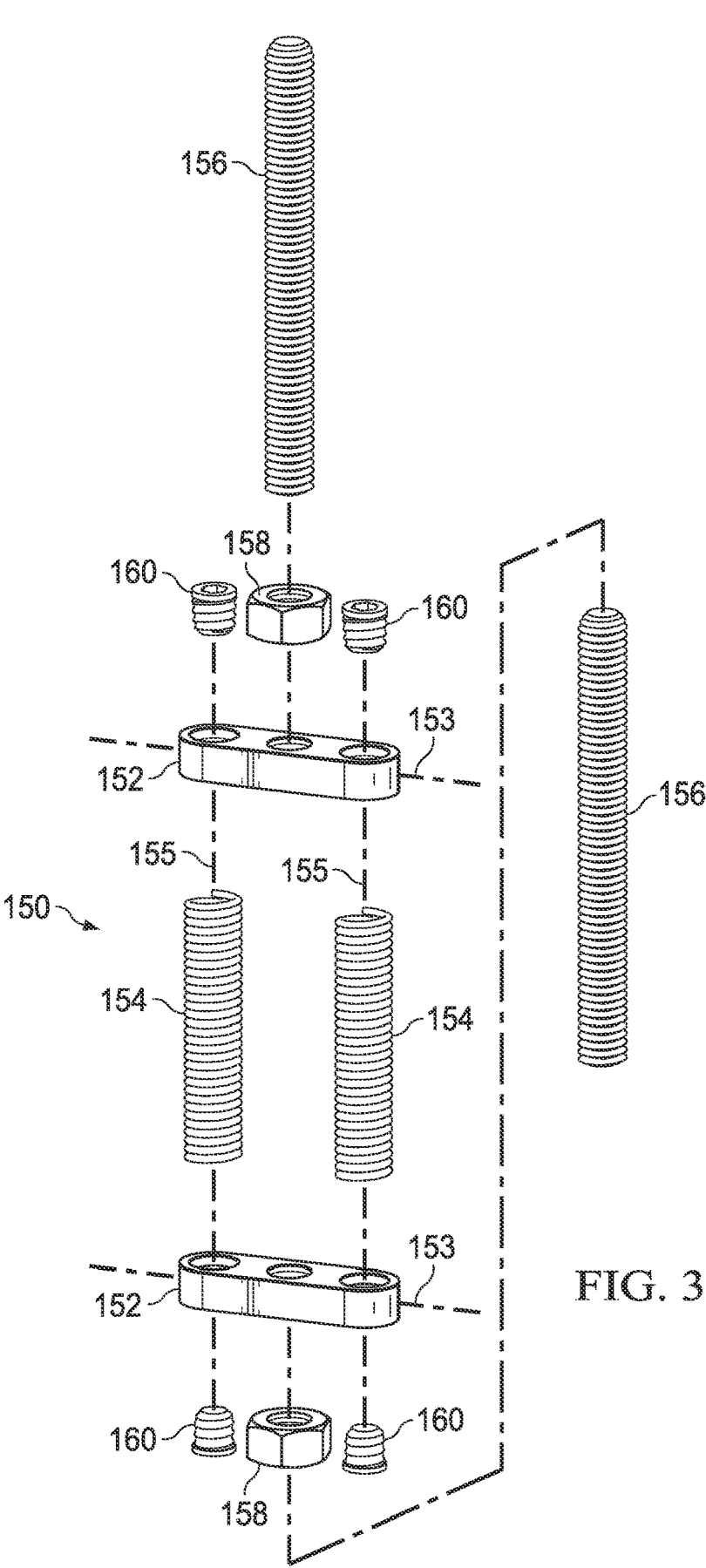
FIG. 3 is an exploded view of a spring hinge similar to that of FIGS. 2A and 2B.

FIG. 3 is an exploded view of a spring hinge 150. The coil springs 154 may be spaced apart along a longitudinal axis 153 of each of the base members 152 such that the longitudinal axis 155 of each spring is generally transverse to the longitudinal axes 153 of the base members 152. Connecting bolts 156 may be secured to external fixators (not shown) at their outer ends and second to respective base members 152 at their inner ends with optional nuts 158 helping to prevent the bolts 156 from separating from the base members 152. Coils springs 154 extend between the base members 152 and may be secured thereto as discussed below in relation to FIGS. 4-6, optionally including conical dowels 160.

Figures 4, 5, 6:
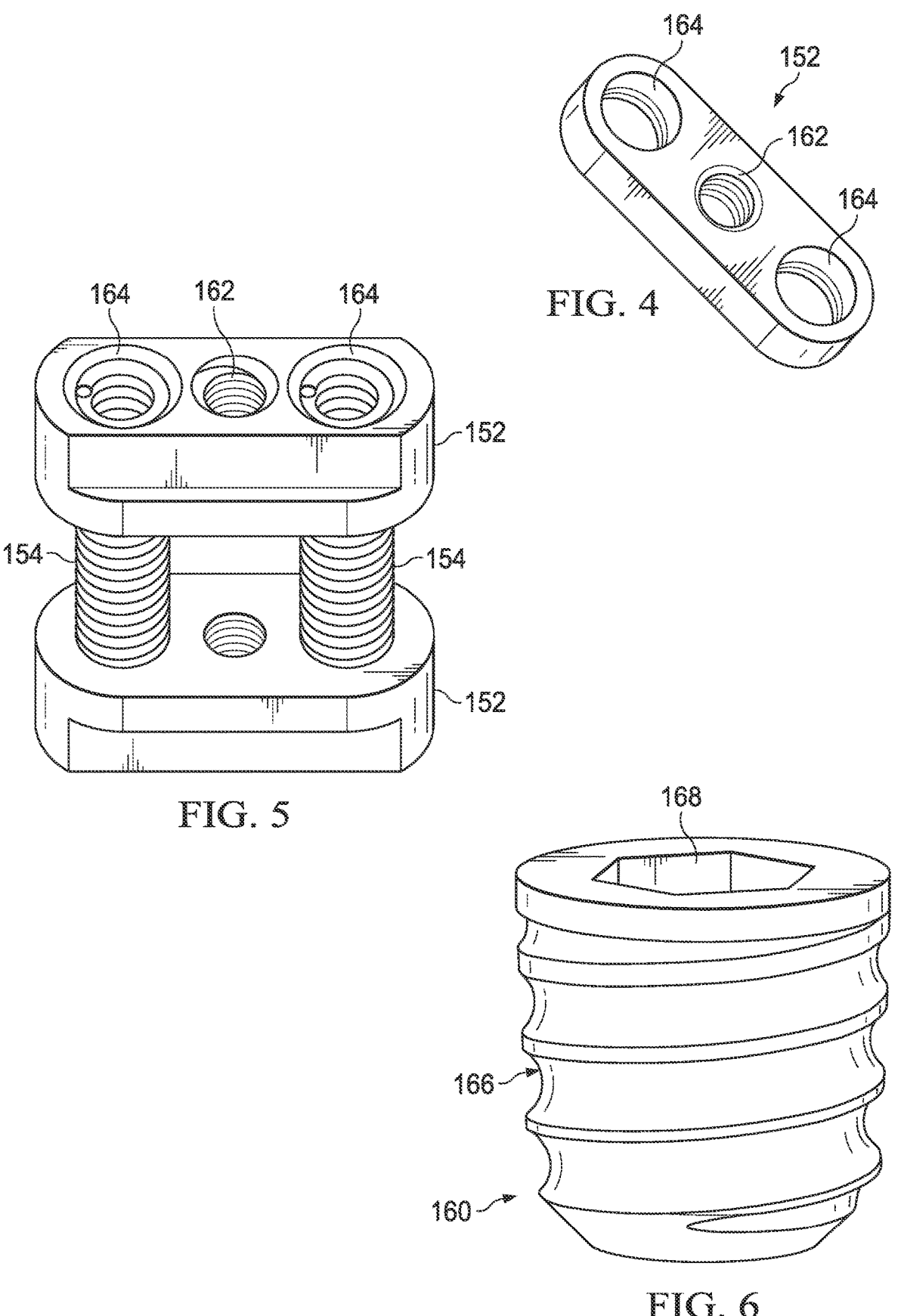
FIG. 4 is a perspective view of a base member as shown in the spring hinge of FIG. 3.
FIG. 5 is a top perspective view of a spring hinge in accordance with the present disclosure.
FIG. 6 is a perspective view of a conical dowel as shown in the spring hinge of FIG. 3.

FIG. 4 illustrates a base member 152 of a spring hinge 150. Base member 152 includes a bolt connection bore 162 centrally disposed to receive a bolt for connecting the spring hinge to an external fixator. As illustrated the bolt connection bore 162 is threaded to receive corresponding threads of a connection bolt such as bolt 156 of FIG. 3. However, it should be appreciated that a connection bolt may be formed integrally with a base member 152 or may be affixed to the base member in any suitable manner. Disposed on either side of the bolt connection bore 162 are spring connection bores 164 configured to receive an end of a spring. In some examples, spring connection bores 164 are threaded with a thread size and pitch corresponding to the coil of a coil spring such that a coil spring may be directly threaded into a spring connection bore 164, as may be seen in FIG. 5. It should be appreciated that positioning spring connection bores 164 and bolt connection bores 162 in a common base member may help shorter the overall functional length (e.g., bending portion) of the spring hinge to allow the spring hinge to be installed in space-limited applications.

Optionally, any suitable fastener may be used to secure a coil spring 154 to a spring connection bore 164. For example, a conical dowel 160 as shown in FIG. 6, may be inserted into a spring connection bore 164 to further secure a coil spring 154 to a base member 152. As shown in FIG. 6, a conical dowel 160 includes an external thread 166 that corresponds to the coil dimensions of a coil spring 154. In this regard, a conical dowel 160 may be threaded into the lumen formed in a coil spring 154. For example, the illustrated embodiment of conical dowel 160 includes a tool-receiving recess 168 for rotating conical dowel 160 as it is threaded into an end of a coil spring 154 disposed in a spring connection bore 164 of a base member 152. The conical shape of the conical dowel 160 causes the conical dowel to exert an increasing radially-directed compression force on the coil spring 154 as the conical dowel is threaded into the lumen of the spring, the spring being radially confined by the base member 152. Base member 152 of FIG. 4 may represent both base members of the spring hinge 150 of FIGS. 1-3, but it should be appreciated that in some embodiments, an upper base member and a lower base member may have different properties or characteristics such as size, shape, features, etc.

Furthermore, it should be appreciated that any suitable means may be used to attach a coil spring 154 to a base member 152. For example, a connection bore 164 may not form an aperture extending entirely through a base member 152 but may instead form a recess extending only partially through a base member. Alternatively, a coil spring may be welded or otherwise adhered to a base member without using a spring connection bore. For example, end caps may be threaded into the coil springs and may be attached to a base member with a bolt or other suitable hardware. For example, U.S. Patent Publication No. 2019/0365420 by Samchukov et al. entitled "ORTHOPEDIC SPRING HINGE SYSTEM AND METHODS THEREOF," which is incorporated by reference herein in its entirety, describes end caps which may be used to install a spring in an external fixation system.

Figures 7, 8, 9:
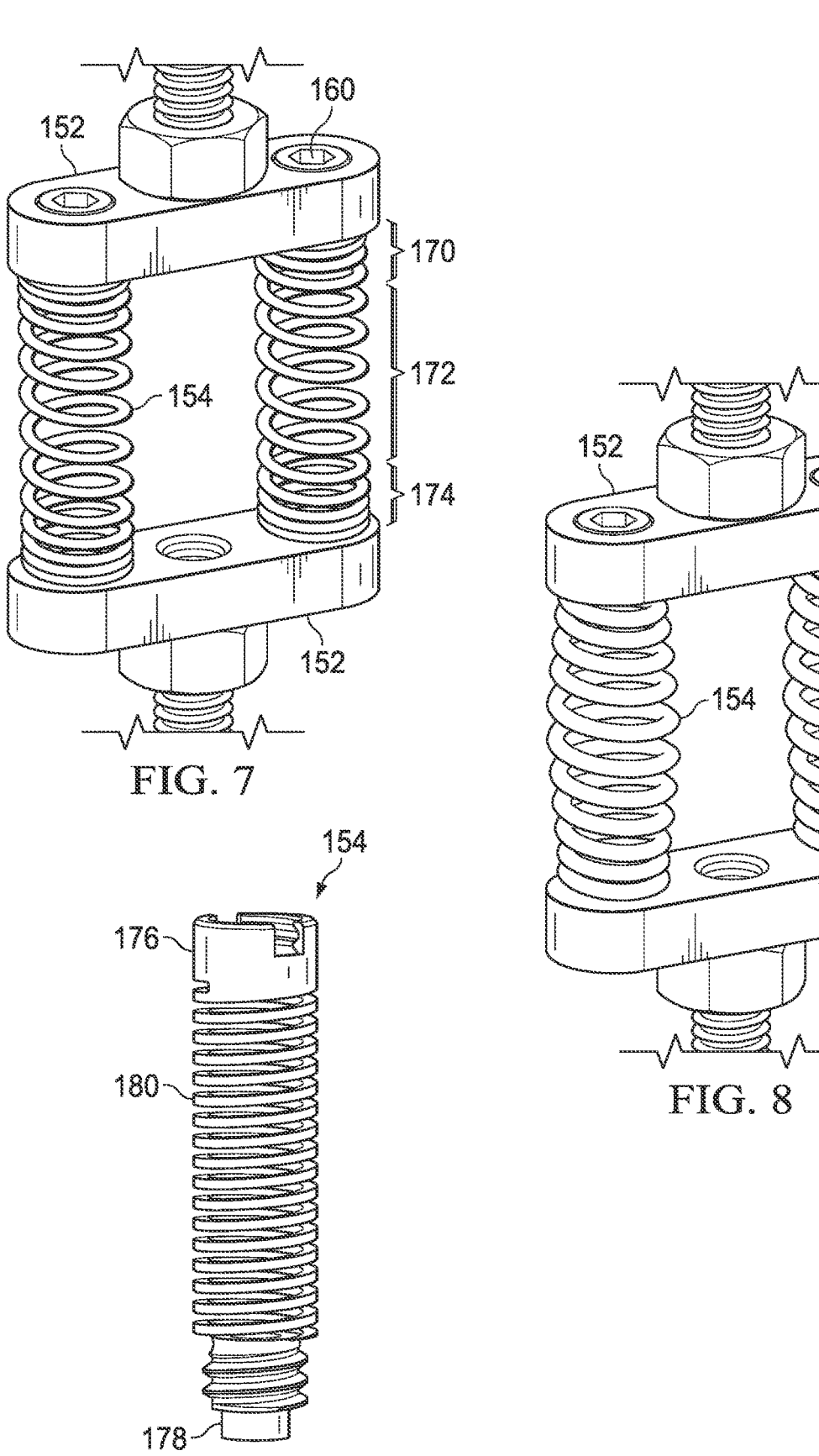
FIG. 7 is a perspective view of a spring hinge in accordance with the present disclosure.
FIG. 8 is a perspective view of a spring hinge in accordance with the present disclosure.
FIG. 9 is a perspective view of a coil spring as may be used in a spring hinge in accordance with the present disclosure.

Rigidity of different springs in a spring hinge can be equal to each other or one (e.g., lateral) spring can be more rigid than the other (e.g., medial) spring. Differential rigidity of two springs can be achieved by using springs having different physical and mechanical properties which impact their bending characteristics. For example, spring length (longer or shorter), spring diameter (larger or smaller), or diameter of spring wire (thinner or thicker). Rigidity of a spring can be the same along the entire length of the spring or some parts of the spring can be less rigid providing a more static rotation axis, leading the anatomical joint to rotate around that axis. Differential rigidity of different parts of a spring can also be achieved by manipulation of spring diameter, coil wrap tightness, diameter of wire, or changing the spring profile (e.g., hourglass profile). The examples of coil springs 154 shown in FIGS. 7 and 8 are constructed with varying physical and mechanical properties along their lengths which impact their bending characteristics. For example, the coil springs 154 of FIG. 7 have a first coil spacing in a first region 170 and a second coil spacing in a second region 172. Further, a third region 174 has a third coil spacing which may be the same as or different that the coil spacing in the first region 170. In the illustrated example, the coil spacing in the first region 170 and the third region 174 is closer or tighter than the coil spacing in the second region 172 disposed between the first region and the second region. In this regard, the tighter coil spacing in the end regions (i.e., first region 170 and third region 174) may provide an increased number of coils for engaging with internal threads in the base member 152 to improve the connection. The wider spacing in the central region 172 may provide a reduced bending resistance of the coil spring 154 in that region. However, it should be appreciated that any number of distinct regions may be used in constructing a coil spring 154 and the respective coil spacings may be closer or further in any region with regard to any other region(s).

The coil springs 154 of FIG. 8 have a first coil diameter in a first region 170 and a second coil diameter in a second region 172. Further, a third region 174 has a third coil diameter which may be the same as or different that the coil diameter in the first region 170. In the illustrated example, the coil diameter in the first region 170 and the third region 174 is smaller than the coil diameter in the second region 172 disposed between the first region and the second region. In this regard, the smaller coil diameter in the end regions (i.e., first region 170 and third region 174) may provide smaller coils for engaging with internal threads in the base member 152. The wider coil diameter in the central region 172 may provide an increased bending resistance of the coil spring 154 in that region. However, it should be appreciated that any number of distinct regions may be used in constructing a coil spring 154 and the respective coil diameters may be smaller or larger in any region with regard to any other region(s).

It should be appreciated that the coil springs 154 of FIGS. 7 and 8 may additionally or alternatively be constructed with other physical and mechanical properties which vary along the length of the coil. For example, in some embodiments, the coil diameter in a central region of a coil spring may be smaller than in regions nearer the ends of the coil spring. As another example, a wire thickness in one or more regions of a coil spring may be greater than a wire thickness in one or more other regions. For example, a coil spring 154 may be constructed using a wire having a greater thickness near its ends than near the center. In this regard, the bending resistance of the coil spring 154 may be reduced in a central region.

Furthermore, it should be appreciated that coil springs 154 may additionally or alternatively be constructed with physical and mechanical properties which vary around the circumference of the coil. For example, in some embodiments, a thickness of the coils may be smaller on one side, or two opposing sides, of the coil spring 154 than on the other side(s). Similarly, the cross-sectional shape of the wire forming the coils may be altered on one or more sides of the coil spring 154. In this regard, bending resistance may be reduced in one or more desired directions while preventing shearing or bending in one or more other directions.

Additionally, while these features have been discussed in relation to coil springs as illustrated in FIGS. 7 and 8, other types of springs disclosed herein may also be constructed in a manner to impart varying physical (e.g., diameter, thickness, width, material, etc.) and mechanical (e.g., spring constant or "k-factor," bending resistance or "rigidity," etc.) properties in different regions of a spring.

As discussed above, the anatomical axis of a joint may change dynamically as the joint pivots. Some anatomical joints are not constrained to a static axis of rotation. That is, when a joint rotates or moves, the corresponding axis of rotation may shift in one or more directions. In this regard, varying the physical and mechanical properties of a spring along its length may facilitate construction of an external fixation system with an axis of rotation that moves dynamically in conjunction with the treated joint.

FIG. 9 illustrates a further example of a coil spring 154 in accordance with the present disclosure. Coil spring 154 of FIG. 9 has an integrated first connector 176 and/or an integrated second connector 178. The coil spring 154 of FIG. 9, including the integrated first and second connectors 176,178, may be monolithically formed from a cylindrical tube. For example, mechanical or electro-chemical cutting may be used to form a coil spring 154 from a cylindrical blank. Although a coil spring according to the present disclosure may be constructed from a coiled cylindrically-shaped wire, the cross-sectional profile of a wire can be modified as shown in FIG. 9, for example, to provide a desired bending elasticity in the plane of hinge movement (e.g., sagittal plane) while maintaining rigidity against undesired movements (e.g., translational shear movements in a horizontal plane).

First connector 176 may include a head having internal threads which facilitate attachment of the coil spring 154 to an external fixation system. For example, a bolt disposed within a base member (e.g., base member 152 of FIG. 4) may be threaded into the head of the first connector 176. In some embodiments, the coil spring 154 may include threads corresponding to such a bolt on the internal wall formed by the coils 180. In this regard, the bolt may be threaded into the coiled portion of the coil spring 154.

Second connector 178 may include external threads which may be threaded directly into corresponding threads of a base member. In some embodiments, a coil spring 154 may include two first connectors 176 or two second connectors 178 (one at each end). Further, in some embodiments, one or both of the first connector 176 and the second connector 178 may be separate and distinct components secured to the coils 180.

The coil spring 154 of FIG. 9 includes wire which has a square or rectangular cross-section. The height and/or width of this cross-section may be altered to impart desired physical or mechanical properties into the spring hinge 150.

While the illustrated examples of coil springs herein include cylindrical coil springs with wires having circular or rectangular cross-sections, it is contemplated that alternative coil spring shapes and wire cross-sections may be used. For example, U.S. Patent Publication No. 2019/0365420 by Samchukov et al. entitled "ORTHOPEDIC SPRING HINGE SYSTEM AND METHODS THEREOF," which is incorporated by reference herein in its entirety, includes a number of alternative spring shapes and wire cross-sections which may help resist shearing movement.

Further, it should be appreciated that the illustrated state of the coil springs 154 shown in FIGS. 7-9 may be a resting (e.g., "relaxed," "unexpanded," or "neutral") state in some embodiments or may be an expanded state in which the base members 152 are pulled apart such that the coil springs 154 are in tension.

Figures 10, 11:
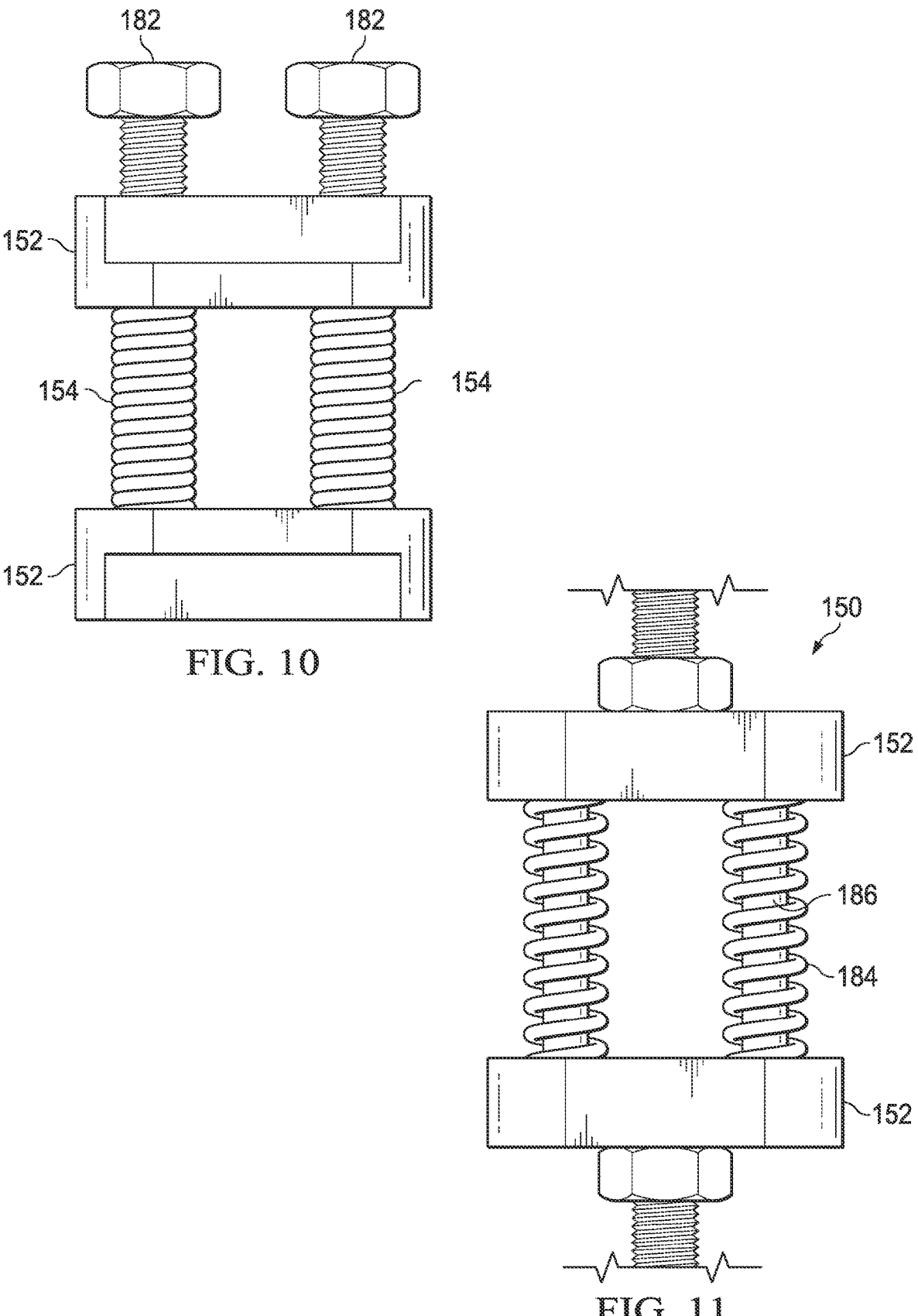
FIG. 10 is a front view of a spring hinge having an adjustable bending length in accordance with the present disclosure.
FIG. 11 is a front view of a spring hinge having primary springs and secondary springs in accordance with the present disclosure.

Differential rigidity of a spring hinge can also be achieved by relative shortening or lengthening of the bending portion of the spring using, for example, threaded components (e.g., bolts or short threaded rods) inserted inside the spring. FIG. 10 illustrates that an adjustment bolt 182 may be selectively extended into or withdrawn from one or more springs of spring hinge 150. The portion of a coil spring 154 in which an adjustment bolt 182 is positioned may be prevented from bending due to the bending resistance of the adjustment bolt 182, which may be substantially greater than the bending resistance of a coil spring 154. In this regard, spring hinge 150 may be configured to have an adjustable bending length. Threading an adjustment bolt 182 further into a coil spring 154 may reduce the length of a portion of the coil spring which is permitted to bend and may, in turn, increase the bending resistance of the external fixation system. In contrast, threading an adjustment bolt 182 further outward from a coil spring 154 may increase the length of the portion of the coil spring which is permitted to bend and may, in turn, decrease the bending resistance of the external fixation system.

This adjustability may allow a user to selectively alter the rigidity of the external fixation system during different phases of treatment. For example, after initially installing an external fixation system around a patient's joint, it may be desirable for one or more adjustment bolts 182 to be fully inserted into a corresponding one or more coil springs 154 to maximize bending resistance and increase rigidity of the system. After a first period of treatment, it may be desirable to partially retract the adjustment bolts 182 to provide an intermediate degree of bending resistance. After a second period of treatment, it may be desirable to completely remove the adjustment bolts 182 to minimize the bending resistance to the inherent resistance provided by the coil springs 154.

In some examples, an adjustment bolt 182 may be configured to be directly threaded into the coils of a coil spring 154. In other examples, an adjustment bolt 182 may be configured to be threaded into a conical dowel which has a lumen extending through its length to accommodate the adjustment bolt such that the adjustment bolt 182 is indirectly secured within the coil spring 154.

FIG. 11 illustrates an example of spring hinge 150 having primary springs 184 and secondary springs 186 extending between the base members 152. In some embodiments, a secondary spring 186 may be disposed within a central cavity of a primary spring 184. For example, the secondary spring 186 may have an outer width that is smaller than the inner width of the central cavity of the primary spring 184 and may have a length similar to or less than a length of the primary spring 184. In other embodiments, the secondary spring 186 may have a length exceeding the length of the primary spring 184. The secondary spring 186 may be positioned such that the secondary spring 186 and the primary spring 184 are concentric with one another. The secondary spring 186 and the primary spring 184 may share the same lengthwise axis.

One or both of a primary spring 184 and a secondary spring 186 may be substantially the same as any embodiment of a coil spring 154 described herein. Additionally or alternatively, one or both of a primary spring 184 and a secondary spring 186 may be substantially the same as any embodiment of other types of springs described herein. In some embodiments, a primary spring 184 may be a coil spring and a secondary spring 186 may be an elastic structure (e.g., plastic or polymer rod) insertable into the primary spring 184. Such an elastic structure may complement or supplement the mechanical properties of the primary spring 184, for example, to increase bending resistance of the spring hinge 150. In some embodiments, a plurality of elastic structures may be provided, and a user may adjust the rigidity of the external fixation system by removing a secondary spring 186 and replacing it with another secondary spring 186 having different physical and mechanical properties. Further in this regard, a plurality of different secondary springs 186 may be used simultaneously to vary the rigidity of a spring hinge 150 at one primary spring 184 as compared to another primary spring (e.g., left and right primary springs may be complemented with secondary springs having different properties) to favor certain bending planes of the external fixation system.

Figure 12:
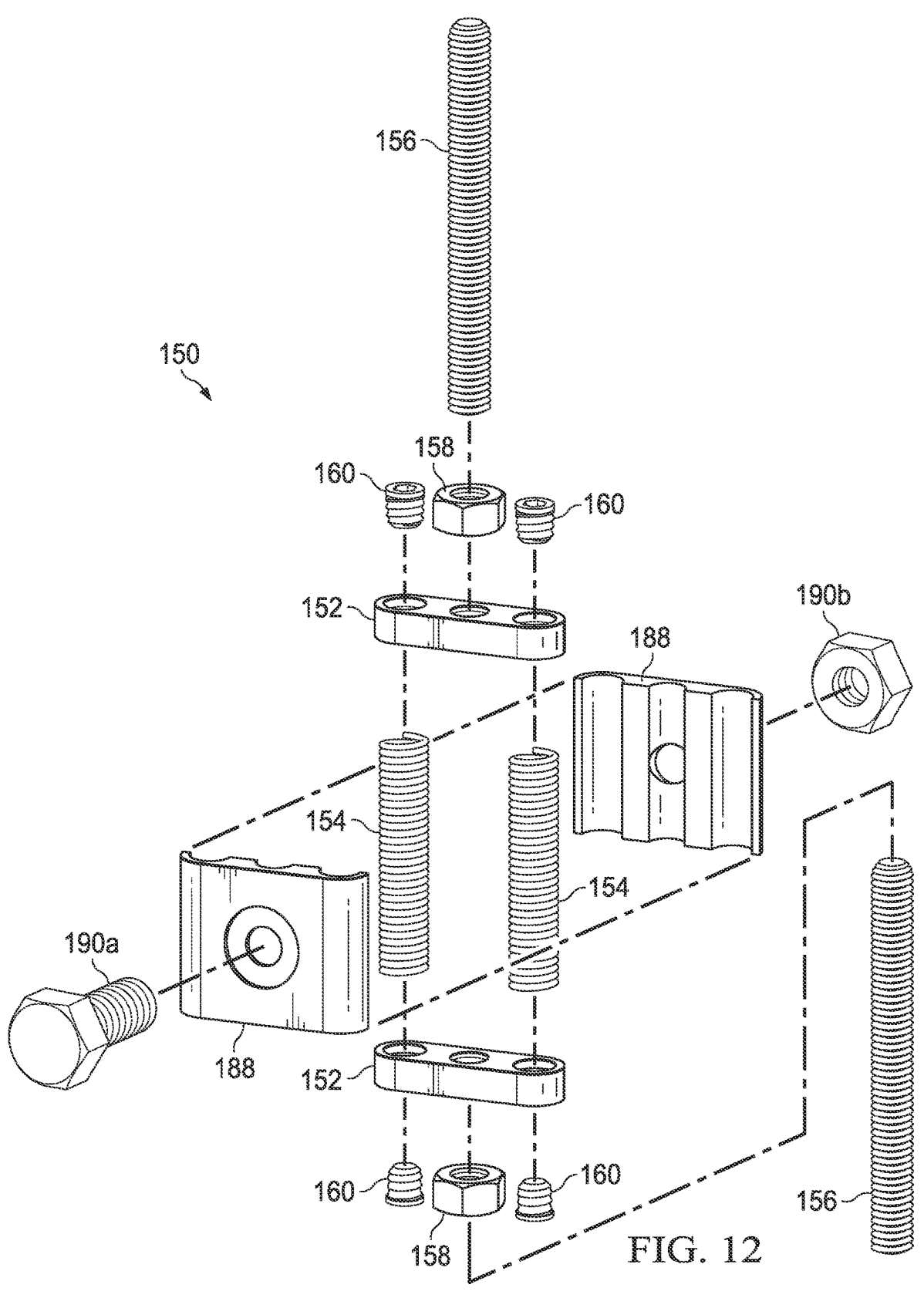
FIG. 12 is an exploded view of a spring hinge with a locking structure in accordance with the present disclosure.

To stabilize an anatomical joint and substantially or completely reduce its motion (e.g., to keep the joint in a certain orientation as may be needed for walking), motion of a spring hinge can be blocked (or "locked"). FIG. 12 is an exploded view of a spring hinge with a locking structure in accordance with the present disclosure. The spring hinge 150 of FIG. 12 may be substantially the same as the spring hinge of FIG. 3. In this regard, reference numerals have not been repeated to avoid obfuscating the illustration. The spring hinge 150 of FIG. 12 includes a locking structure configured to lock the spring hinge 150 in place and prevent bending. In the illustrated example of FIG. 12, the locking structure 188 comprises a first locking plate and a second locking plate 188. The first and second locking plates 188 may be positioned on either side of the coil springs and base members 152. The first and second locking plates 188 may then be clamped together and secured to the spring hinge with any suitable locking mechanism. In the illustrated embodiment, the locking mechanism includes a locking bolt 190*a* extending through apertures in the locking plates 188 and a locking nut 190*b*.

The locking plates 188 may each include recesses on an inner wall to receive the coil springs 154. Ridges formed between the grooves on the first locking plate 188 may be drawn into contact with corresponding ridges on the second locking plate 188 when the locking structure is installed. The inner surfaces of the base members 152 (e.g., top surface of the lower base member and bottom surface of the upper base member) may rest against opposing end surfaces of the locking plates 188. In this regard, the base members may be prevented from rotating with respect to one another when the locking structure is installed.

Figures 13, 14, 15:
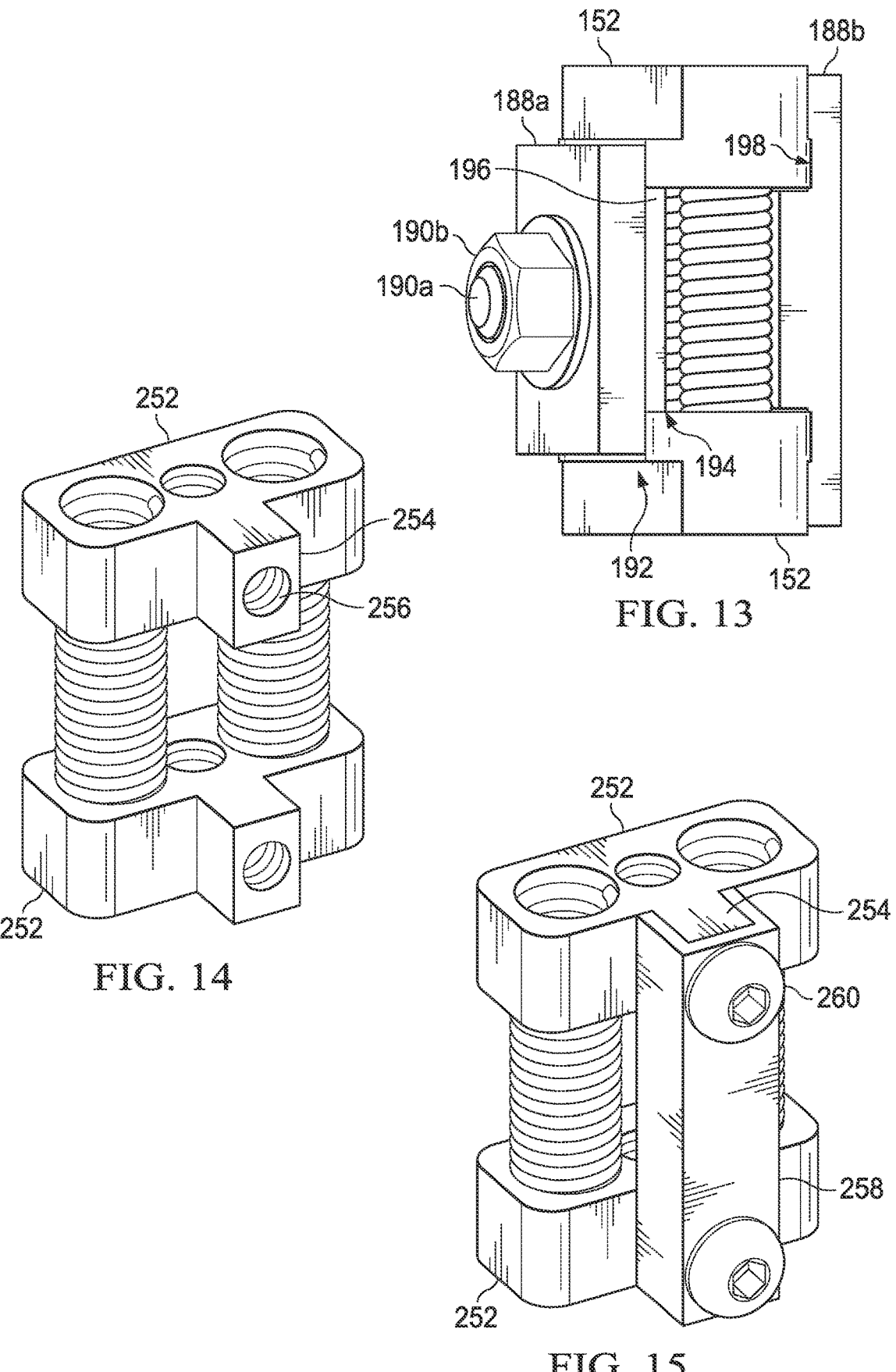
FIG. 13 is a perspective view of a spring hinge with a locking structure in accordance with the present disclosure.
FIG. 14 is a perspective view of a spring hinge having a locking structure in accordance with the present disclosure.
FIG. 15 is a perspective view of the spring hinge of FIG. 14 with a locking plate.

The spring hinge 150 of FIG. 13 may be substantially the same as the spring hinge of FIG. 12 and includes an alternative example of a locking structure configured to lock the spring hinge 150 in place and prevent bending. In the illustrated example of FIG. 13, the first locking plate 188*a* may include a block 196 that extends between a flange 192 of each base member 152. The flanges 192 of each base member 152 may rest on opposing end surfaces of the block 196. In this regard, the flanges may be prevented from moving closer to one another which, in turn, prevents rotation of the base members 152 with respect to one another.

The second locking plate 188*b* may include a transverse groove 198 adjacent each end of the locking plate 188*b* configured to receive the flange 192 of a respective one of the base members 152. The groove 198 may have a height that closely corresponds to the height of the flange 192 such that the flange is closely mated with the locking plate 188*b* on both the upper and lower sides of the flange. In this regard, the base members 152 may be prevented from rotating with respect to one another when the locking structure is installed. It should be appreciated that a locking structure may include two first locking plates 188*a*, two second locking plates 188*b*, or one of each as illustrated.

The spring hinge of FIG. 14 may be substantially the same as the spring hinge of FIG. 3 with an alternative example of a locking structure configured to lock the spring hinge in place and prevent bending. In the illustrated example of FIG. 14, the locking structure comprises a lock plate receiver 254 on each base member 252. The lock plate receivers 254 illustrated in FIG. 14 comprise a cuboidal protrusion extending from a front or rear surface of a respective base member 252 which includes a lock bore 256. However, it should be appreciated that a lock plate receiver 254 may have any suitable configuration. In some embodiments, a lock plate receiver 254 may simply comprise a lock bore 256 extending into the planar front or rear surface of the base member 252.

As shown in FIG. 15, a lock plate 258 may be secured to the lock plate receiver 254 of each base member 252 with one or more lock bolts 260 disposed in the lock bores 256. In some embodiments, a notch may be cut into the side of the lock plate such that the lock plate can be slid off the base members to a side when the lock bolts are loosened. The lock plate 258 may rigidize the spring hinge and prevent rotation of the base members 252 with respect to one another. In the illustrated embodiment, the lock plate 258 comprises a C-shaped plate that extends around three sides of each lock plate receiver 254. However, any suitable shape (e.g., L-shaped plate) may be used without departing from the scope of this disclosure. For example, a flat plate may extend from the lock bore 256 of one base member to the other, as may be appropriate in an embodiment in which the locking plate receivers 254 are integrated into the planar front or rear surface of base member 152 of FIG. 4.

Figure 16:
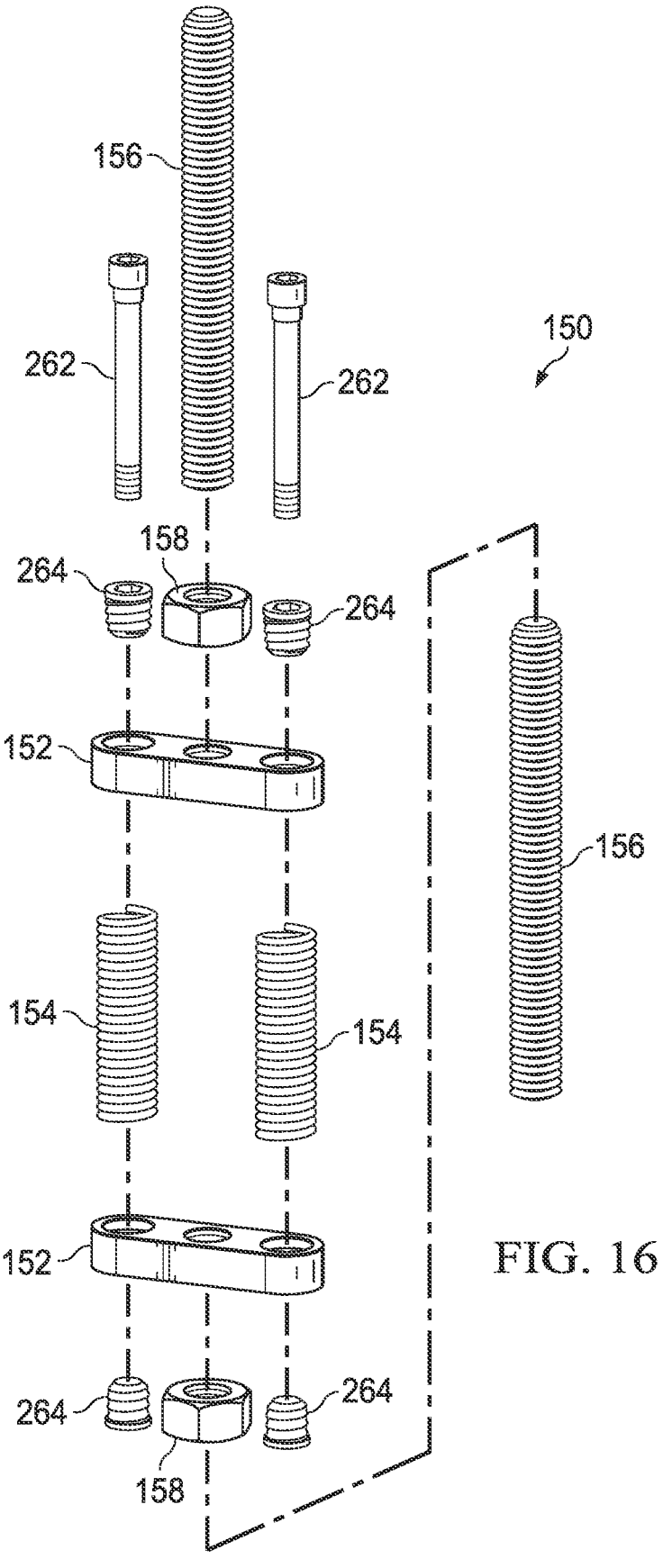
FIG. 16 is an exploded view of a spring hinge with a locking structure in accordance with the present disclosure.
Figures 17, 18:
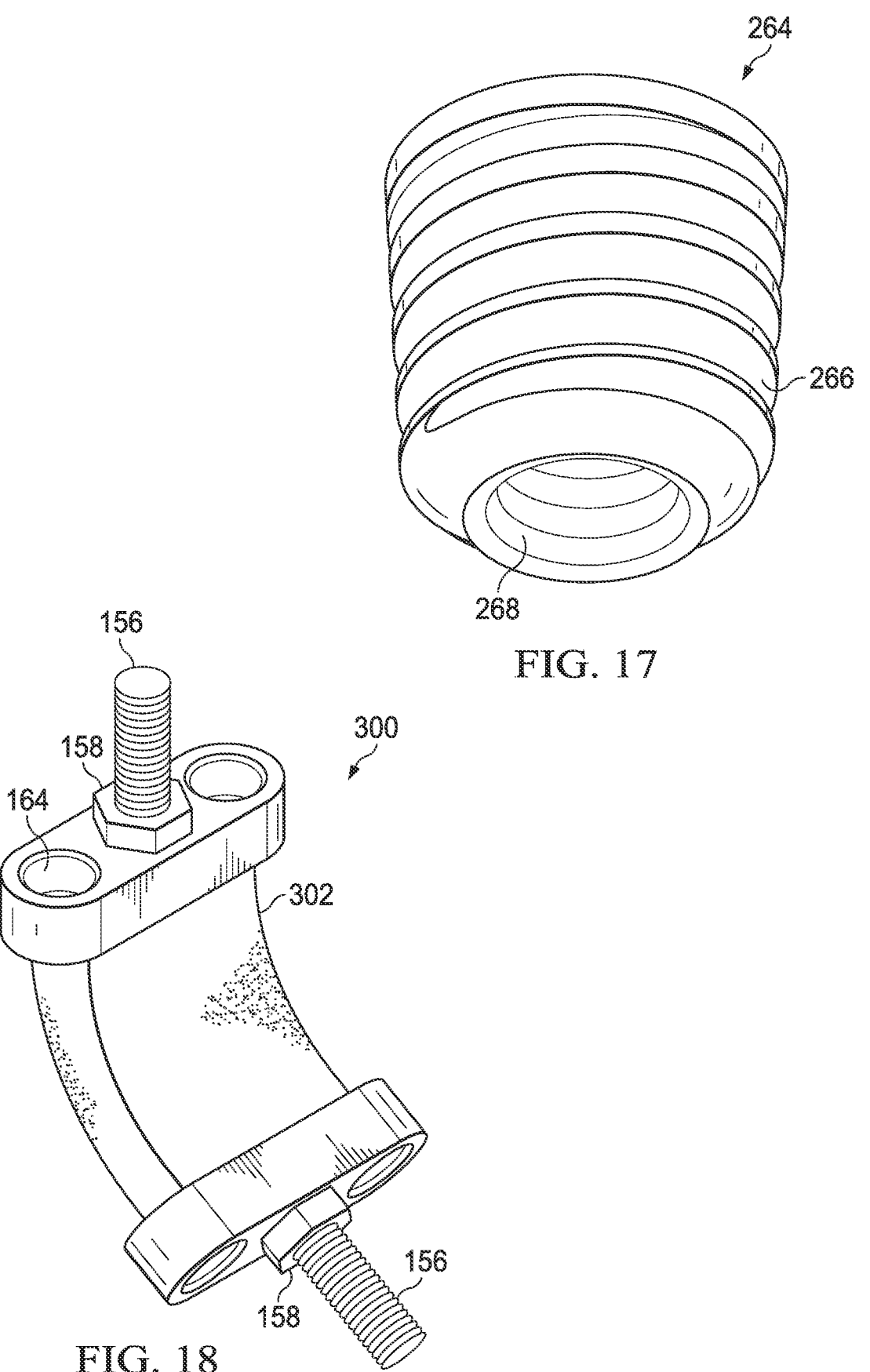
FIG. 17 is a perspective view of a conical dowel as shown in the spring hinge of FIG. 16.
FIG. 18 is a perspective view of a spring hinge in accordance with the present disclosure in a flexed configuration.

FIG. 16 is an exploded view of a spring hinge with an alternative locking structure comprising tie rods 262. The spring hinge 150 may be substantially the same as the spring hinge illustrated in FIG. 3. Conical dowels 264 include an external thread 266 to engage the springs 154 or base members 152 as shown in FIG. 17. Conical dowels 264 may also include an internal thread 268 on a central bore to engage corresponding threads of the tie rods 262. For example, in the illustrated embodiment, the lower end of the tie rods 262 may be threaded to engage the lower dowels 264. In another example, both ends of the tie rods may be threaded to engage respective conical dowels 264. That is, in some embodiments, hinge motion can be blocked by placement of threaded components (e.g., standard threaded rod) inside one or both of the springs 154. In that regard, the shape and diameter of the internal thread of the spring may match the external thread of a tie rod 262.

A tie rod 262 may include a head with a larger external diameter to prevent the head from entering the central bore of a respective conical dowel 264. A tool-engagement feature such as a hexagonal tightening countersink may be provided in one or more conical dowels 264. Additionally or alternatively, external knurling may be provided on a surface of a tie rod 262 for a manual grip.

Figures 21, 22:
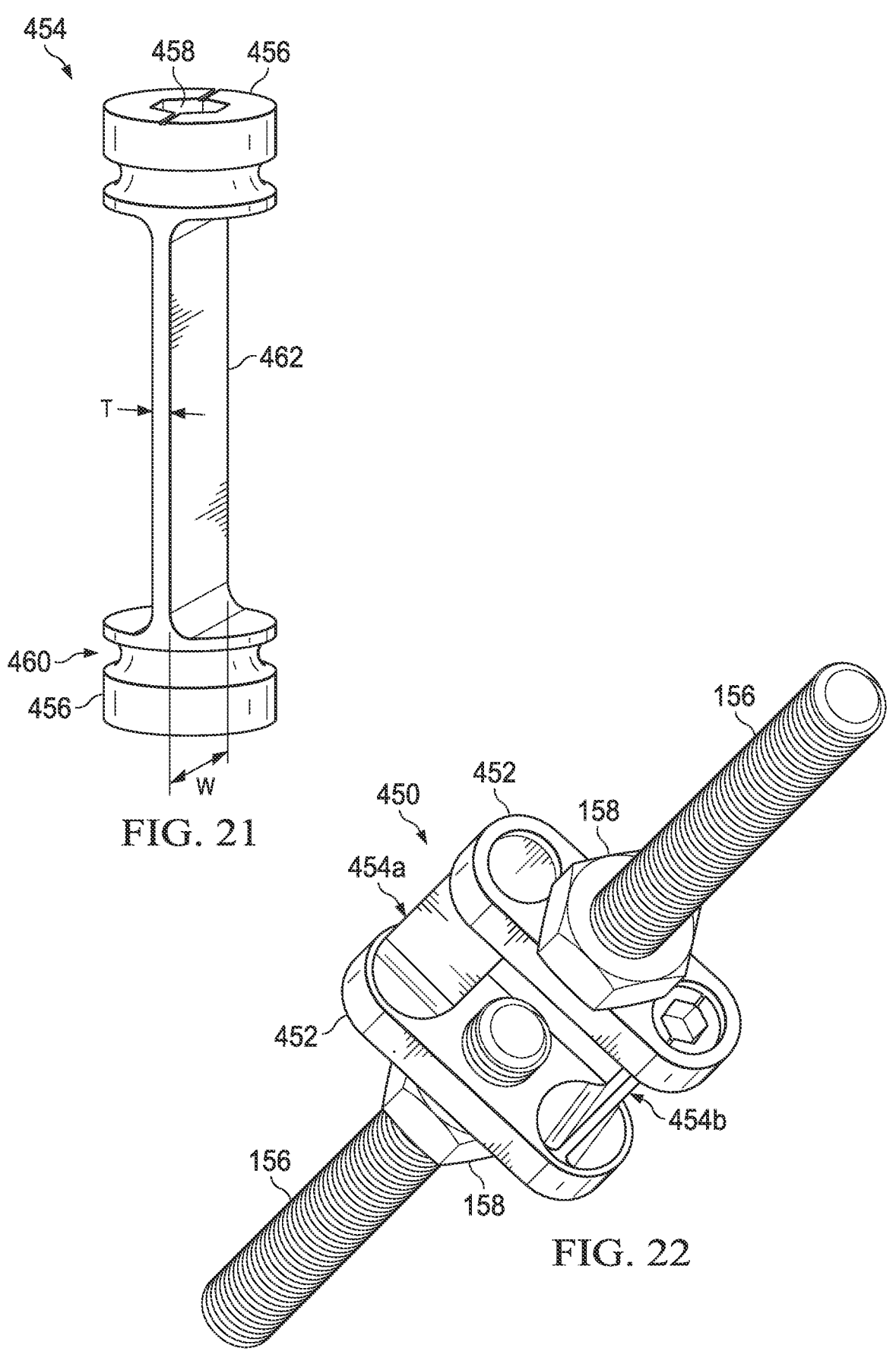
FIG. 21 is a perspective view of a blade spring as may be used in a spring hinge in accordance with the present disclosure.
FIG. 22 is a perspective view of a spring hinge including the blade spring of FIG. 21 in accordance with the present disclosure.
Figure 23:
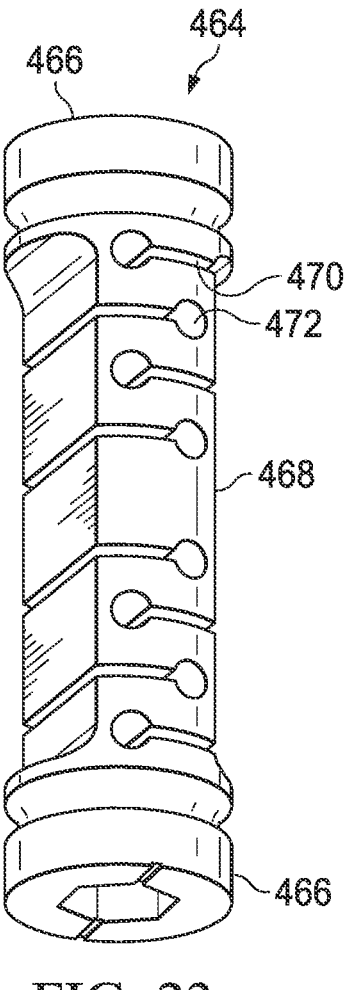
FIG. 23 is a perspective view of a slotted spring as may be used in a spring hinge in accordance with the present disclosure.
Figure 24:
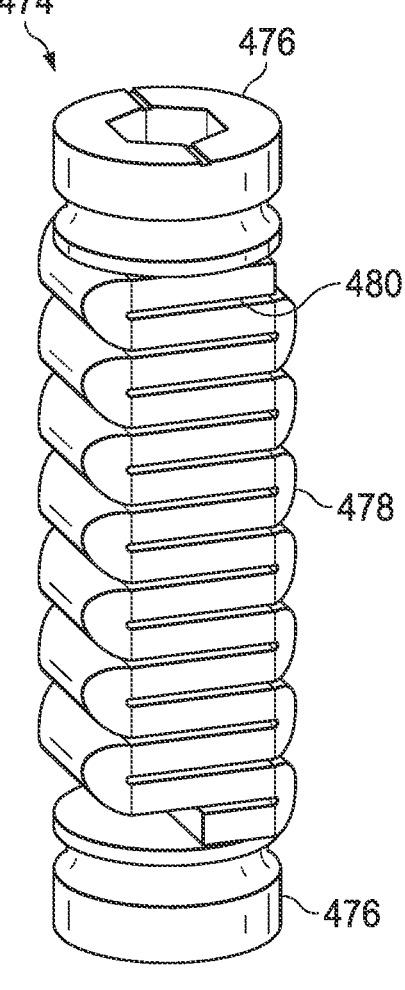
FIG. 24 is a perspective view of a ribbon spring as may be used in a spring hinge in accordance with the present disclosure.

Although illustrated in FIGS. 12-17 in the context of coil springs, it should be appreciated that the locking structures described herein may be similarly applicable to other spring types including, but not limited to, a flexible spring 302 as in FIG. 18, a blade spring as in FIG. 21, a slotted spring 464 as in FIG. 23, a ribbon spring as in FIG. 24, or the spring hinge designs of FIGS. 25-32.

FIG. 18 is a perspective view of a spring hinge 300 in accordance with the present disclosure having a flexible spring 302 in a flexed configuration. An elastic or super-elastic material such as a polymer or other elastomeric material may be utilized to construct such a flexible spring 302. In the illustrated embodiment, the cross section of flexible spring 302 is generally rectangular providing elastic bending in one plane (e.g., sagittal plane) while preventing (minimizing) bending in the orthogonal plane (e.g., coronal plane). In the illustrated example, the flexible spring 302 is formed as a single blade of material. However, it should be appreciated that a plurality of flexible springs 302 each formed of separate blades may be provided in a spring hinge 300.

Figures 19, 20:
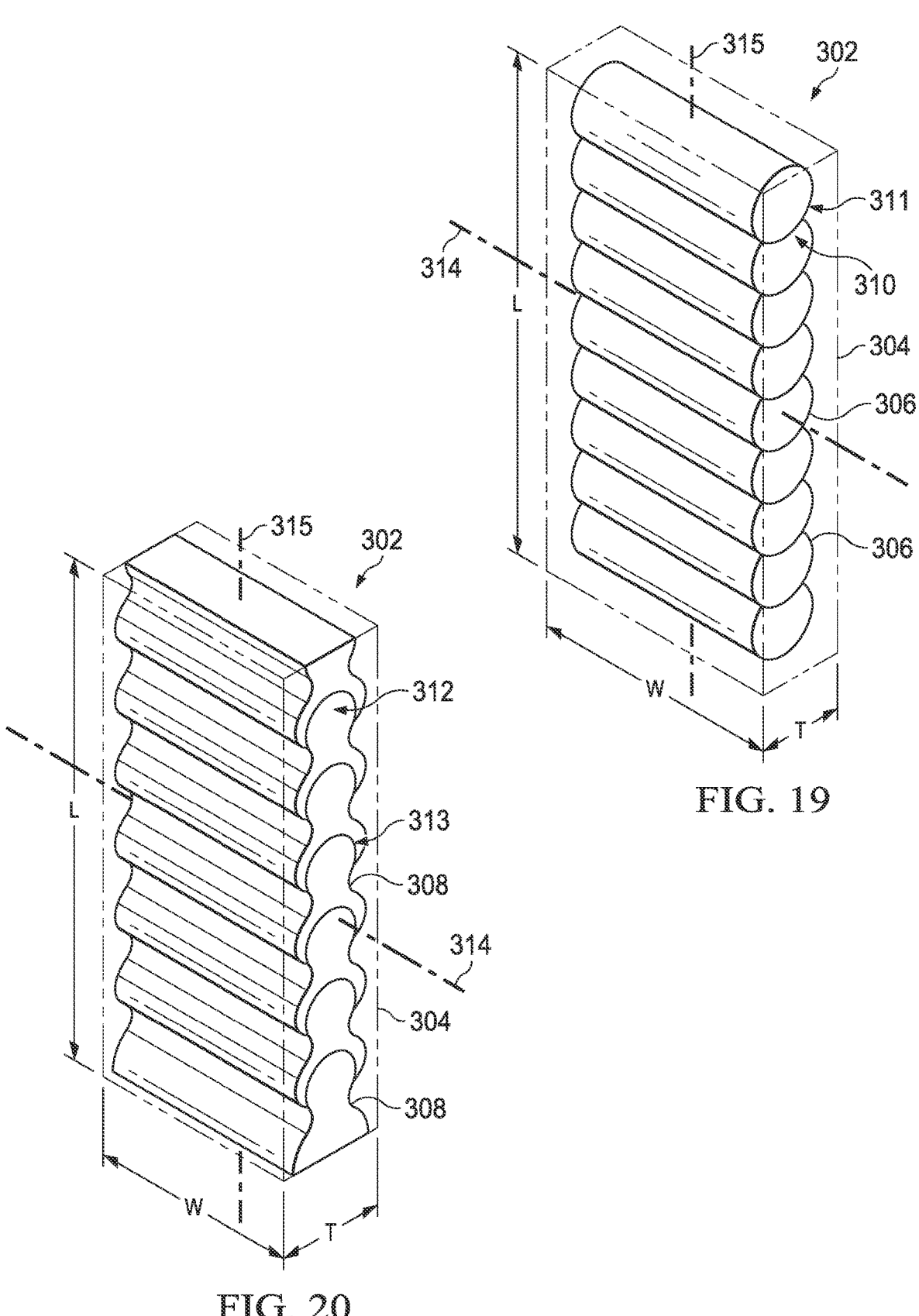
FIG. 19 is a perspective view of a flexible spring as may be used in a spring hinge in accordance with the present disclosure.
FIG. 20 is a perspective view of a flexible spring as may be used in a spring hinge in accordance with the present disclosure.

FIG. 19 is a perspective view of a flexible spring 302 as may be used in a spring hinge in accordance with the present disclosure. A plurality of rigid hinge members 306 may be arranged in series with corresponding features to facilitate bending in a desired direction. Each hinge member 306 may include a recess in the shape of a concave groove 310 extending along a longitudinal length of the hinge member 306 and may include a convex outer surface 311 corresponding to a shape of the groove 310 for engagement with an adjacent hinge member. The hinge members 306 may be made of aluminum or other rigid material and encased in an elastomer 304 to provide anatomical joint rotation in conjunction with pivoting of the flexible spring 302 about rotation axis 314 (which may translate dynamically with the anatomical joint) while resisting torsion about longitudinal axis 315 due to the rigid hinge member 306 which constrain such rotation. If some amount of torsion about longitudinal axis 315 is desired, the hinge members 306 may be constructed of less rigid material than aluminum. Flexible spring 302 may have a height or length L, a width W, and thickness T. The flexible spring 302 may be configured to prevent bending of the spring hinge within a plane in which the height and width of the flexible spring extend, and to permit bending of the spring hinge within a plane in which the height and thickness of the flexible spring extend.

FIG. 20 is a perspective view of an alternative embodiment of flexible spring 302 as may be used in a spring hinge in accordance with the present disclosure. In the embodiment of FIG. 20, each rigid hinge member 308 may include a ridged convex protrusion 312 configured for mating engagement with a corresponding convex slot 313 formed between opposing arms of an adjacent hinge member 308.

FIG. 21 is a perspective view of a blade spring 454 as may be used in a spring hinge in accordance with the present disclosure. The blade spring 454 includes a spring head 456 on each end configured to mate with a corresponding base member. One or both spring heads 456 may optionally include a tool-receiving recess 458 for use in spring hinges in which the blade spring 454 is rotatable, as discussed below in relation to FIG. 22. Each spring head 456 may also include a circumferential groove 460 configured to receive an O-ring to mate the blade spring 454 with a base member at each end. A flexible blade 462 having a thickness T and a width W extends longitudinally between the first and second spring heads 456. The blade spring 454 is configured to facilitate bending in the direction the thickness extends and to resist or prevent bending in the direction in which the width extends.

FIG. 22 is a perspective view of a spring hinge 450 including two blade springs 454a, 454b similar to those of FIG. 21. In the illustrated example, two blade springs 454a, 454b (e.g., medial/lateral) are assembled into spring hinge 450 such that the first blade spring 454a is attached to the base members 452 in a fixed position while the second blade spring 454b is pivotably connected to the base members 452. As shown, the second blade spring 454b is oriented transversely with respect to the first blade spring 454a and the direction of bending of the spring hinge 450, thereby blocking the movement of the spring hinge. The second blade spring 454b may be rotated 90° via the tool-receiving recess 458 to align the flexible blade 462 of the blade spring 454b with the first blade spring 454a to permit bending of the spring hinge 450. It will be appreciated that in some embodiments, both blade springs 454a, 454b may be rotatable and in other embodiments, both blade springs may be permanently attached to or integrally formed with the base members 452 such that no rotation along the longitudinal axes of the blade springs is permitted.

FIG. 23 is a perspective view of a slotted spring 464 as may be used in a spring hinge in accordance with the present disclosure. The slotted spring 464 may be formed from a flexible elastic rod forming the spring body 468 which extends between spring heads 466. A plurality of slots 470 are formed into the spring body 468 in a transverse direction from opposing sides. A channel 472 extends across the internal end of each slot 470 may increase the flexibility of the slotted spring 464 in the desired direction. In alternative embodiments, all or a majority of the slots 470 may be formed into the slotted spring 464 from the same side. The channels 472 may also optionally be omitted from one or both sides.

Different bending resistances between an anatomical joint plane of motion and orthogonal planes of the spring body 468 can be achieved by altering the particular profile features of the spring body. For example, the width of all or some of the slots 470 may be increased or reduced. Similarly, the diameter of all or some of the channels 472 may also be increased or reduced. The slotted spring 464 may be formed in one-step, such as by casting, 3D printing, or injection molding, or may be formed with the spring body 468 as a solid block with the slots 470 and channels 472 later being cut or drilled into the spring body 468.

FIG. 24 is a perspective view of a ribbon spring 474 as may be used in a spring hinge in accordance with the present disclosure. The ribbon spring 474 may be formed from a flexible ribbon 478 which extends between spring heads 476. A plurality of slots 480 are formed in the ribbon 478 in a transverse direction from opposing sides. The shape of the ribbon 478, may provide flexibility in one plane while resisting rotation in orthogonal planes and resisting axial compression.

Different bending resistances between an anatomical joint plane of motion and orthogonal planes of the flexible rod can be achieved by altering the particular profile features of the ribbon 478. For example, the width of all or some of the slots 480 may be increased or reduced. Similarly, the thickness of the ribbon 478 may be increased to increase bending resistance or reduced to reduce bending resistance. The ribbon spring 474 may be formed in one-step, such as by casting, 3D printing, or injection molding, or may be formed from an elongated ribbon which is folded to form the slots.

Both the slotted spring 464 of FIG. 23 and the ribbon spring 474 of FIG. 24 may be substituted for one or both of the blade spring 454 of FIG. 22. In this regard, the springs 464, 474 each may include a circumferential groove at each for receipt of an O-ring and/or a tool-receiving recess to facilitate rotation. The springs 464, 474 may also be integrally formed with base members 452.

Figures 25, 26:
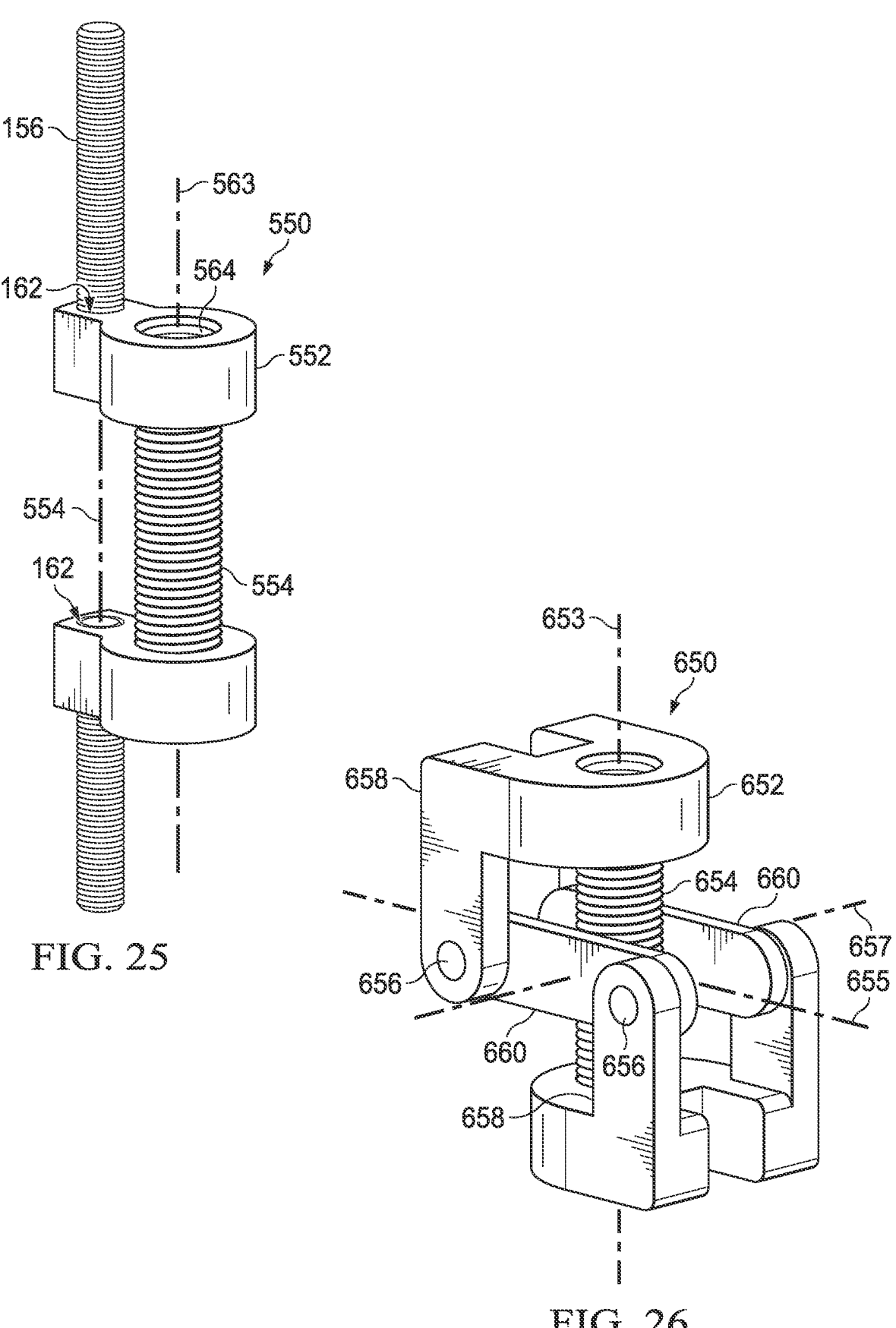
FIG. 25 is a perspective view of a spring hinge in accordance with the present disclosure.
FIG. 26 is a perspective view of a single spring hinge with a double link in accordance with the present disclosure.

FIG. 25 is a perspective view of a spring hinge 550 in accordance with the present disclosure. Spring hinge 550 includes base members 552 each having a bolt connection bore 162 for receiving a bolt 156 or other mechanism for attaching the base members 552 to an external fixation system. Each base member 552 may also have a spring connection hole 564 to receive a respective end of the coil spring 554 (or any other suitable spring type such as those disclosed herein).

The spring hinge 550 may be constructed such that the longitudinal axis 553 of the spring 554 is offset from the longitudinal axis 555 of each of the bolt connection bores 162. Use of a spring 554 with an eccentric bolt (or other mounting rod) orientation may help prevent impingement of joint contacting surfaces (e.g., at the ankle) due to hinge misalignment (e.g., too anterior or too posterior) relative to the joint axis of rotation. The spring hinge 550 may be rotated within an external fixation system about the longitudinal axis 555 to achieve desired alignment (e.g., anterior/posterior position in sagittal plane). In this regard, the eccentric arrangement provides caster-like behavior to allow the spring hinge 550 to self-align as a joint is flexed. Once aligned, the spring hinge 550 can be locked in place. Any residual misalignment may be compensated for by transverse spring deflection.

FIGS. 26-32 illustrate embodiments of spring hinges in accordance with the present disclosure having at least one hinge connector linking the base members at respective ends of one or more springs. A hinge connector may prevent or reduce shear movement in the anterior-posterior and medial-lateral directions and also prevent or reduce rotation about certain axes while permitting rotation or pivoting about a desired axis. Although primarily illustrated with coil springs, it should be appreciated that the concepts of FIGS. 26-32 are equally applicable to other spring types such as those disclosed herein.

FIG. 26 is a perspective view of a single spring hinge 650 with a double link in accordance with the present disclosure. A coil spring 654 extends along a longitudinal axis 653 between two base members 652. Each base member 652 includes two arms 658 extending generally toward the other base member. First and second hinge connectors 660 extend between respective pairs of arms 658 and are secured thereto with a pin joint 656. In this regard, the first base member is secured to the second base member with two hinge connectors 660. Specifically, a first hinge connector 660 extends between a first arm 658 of the first base member 652 and a second arm of the second base member, and a second hinge connector extends from a third arm of the first base member to a fourth arm of the second base member. The first and second hinge connectors are both disposed internally with respect to the arms 658. That is, a first end of the first hinge connector and a first end of the second hinge connector are both disposed in between the first arm and third arm of the first base member. A second end of the first hinge connector and a second end of the second hinge connector are both disposed in between the second arm and the fourth arm of the second base member.

The hinge connectors 660 and associated pin joints 656 prevent rotation of the spring hinge 650 (e.g., between the two base members) about the longitudinal axis 653 and first transverse axis 655 but facilitate rotation of the spring hinge 650 about the second transverse axis 657. The hinge connectors 660 also prevent translation in planes parallel to the transverse axes. The first and second base members 652 are configured to be secured to an external fixation system such that a longitudinal axis of the hinge connector (parallel to axis 655 in the illustrated embodiment) is parallel to a plane in which an anatomical joint encompassed by the external fixation system rotates. The spring hinge 650 is configured such that the axis of rotation 657, as the spring hinge bends in the plane in which the first transverse axis 655 and longitudinal axis 653 are disposed, translates dynamically in conjunction with translation of an anatomical axis of rotation of the treated joint.

Figures 27, 28:
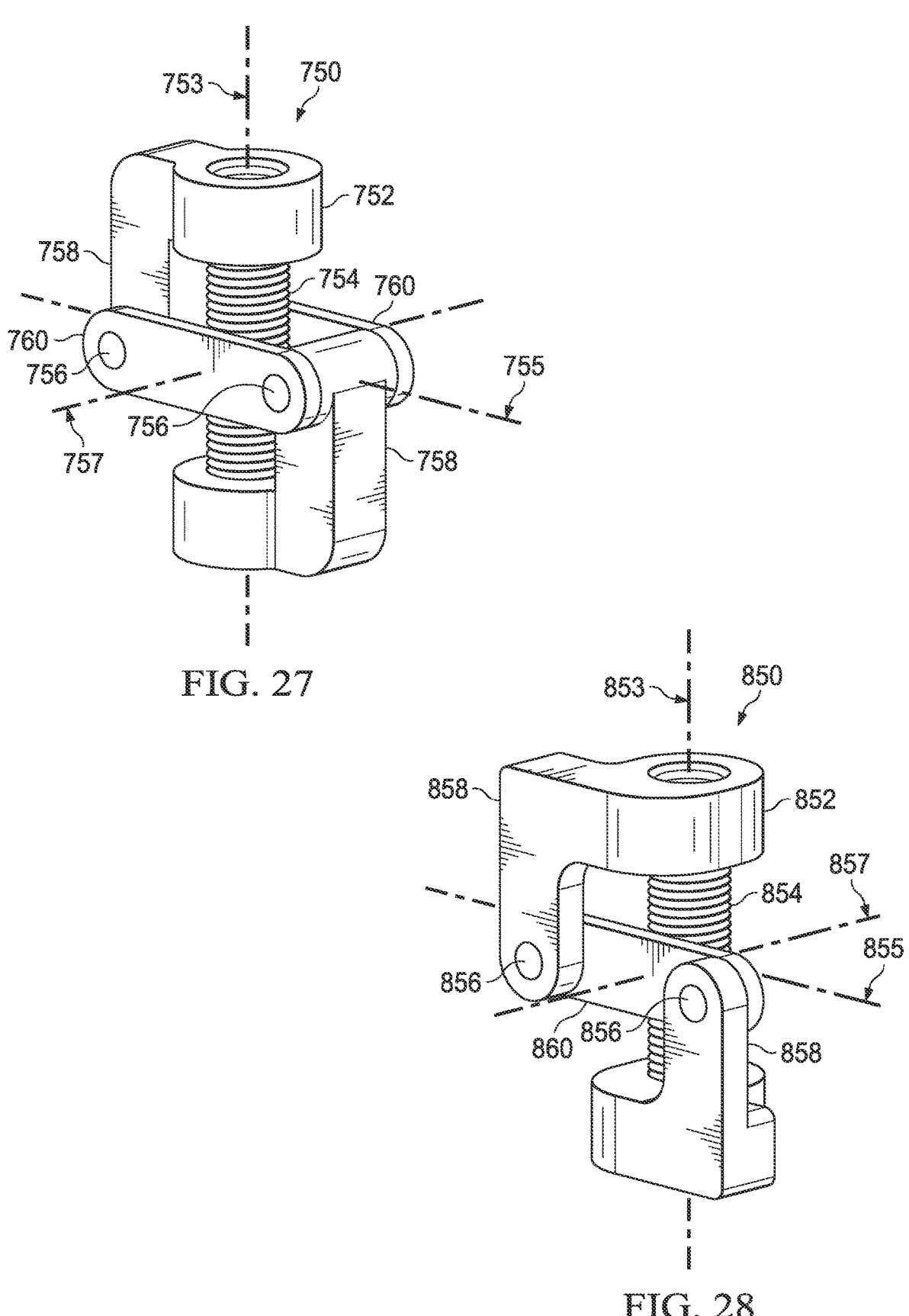
FIG. 27 is a perspective view of a single spring hinge with a double link in accordance with the present disclosure.
FIG. 28 is a perspective view of a single spring hinge with a single link in accordance with the present disclosure.

FIG. 27 is a perspective view of a single spring hinge 750 with a double link in accordance with the present disclosure. A coil spring 754 extends along a longitudinal axis 753 between two base members 752. Each base member 752 includes an arm 758 extending generally toward the other base member. That is, the arm 758 of the lower base member 752 extends generally upward and the arm 758 of the upper base member 752 extends generally downward. First and second hinge connectors 760 extend between respective pairs of arms 758 and are secured thereto with a pin joint 756. In this regard, the first base member is secured to the second base member with two hinge connectors 760. Specifically, a first hinge connector 760 extends between a first arm of the first base member and a second arm of the second base member, and a second hinge connector 760 also extends between the first arm of the first base member and the second arm of the second base member. The first and second hinge connectors are both disposed externally with respect to the arms 758. That is, a first end of the first hinge connector and a first end of the second hinge connector are disposed on opposing sides of the first arm. A second end of the first hinge connector and a second end of the second hinge connector are disposed on opposing sides of the second arm.

The hinge connectors 760 and associated pin joints 756 prevent rotation of the spring hinge 750 (e.g., between the two base members) about the longitudinal axis 753 and first transverse axis 755 but facilitate rotation of the spring hinge 750 about the second transverse axis 757. The hinge connectors 760 also prevent translation in planes parallel to the transverse axes. The first and second base members 752 are configured to be secured to an external fixation system such that a longitudinal axis of the hinge connector (parallel to axis 755 in the illustrated embodiment) is parallel to a plane in which an anatomical joint encompassed by the external fixation system rotates. The spring hinge 750 is configured such that the axis of rotation 757, as the spring hinge bends in the plane in which the first transverse axis 755 and longitudinal axis 753 are disposed, translates dynamically in conjunction with translation of an anatomical axis of rotation of the treated joint.

FIG. 28 is a perspective view of a single spring hinge 850 with a single link in accordance with the present disclosure. A coil spring 854 extends along a longitudinal axis 853 between two base members 852. Each base member 852 includes an arm 858 extending generally toward the other base member. That is, the arm 858 of the lower base member 852 extends generally upward and the arm 858 of the upper base member 852 extends generally downward. A hinge connector 860 extends between the arms 858 and is secured thereto with a pin joint 856. In this regard, the first base member is secured to the second base member with the hinge connector 860. Although shown with the hinge connector disposed internally with respect to the arms 858, that is between the arms 858 and the coil spring 854, the hinge connector 860 could alternatively be disposed externally with respect to the arms.

The hinge connector 860 and associated pin joints 856 prevent rotation of the spring hinge 850 (e.g., between the two base members) about the longitudinal axis 853 and first transverse axis 855 but facilitate rotation of the spring hinge 850 about the second transverse axis 857. The hinge connector 860 also prevents translation in planes parallel to the transverse axes. The first and second base members 852 are configured to be secured to an external fixation system such that a longitudinal axis of the hinge connector (parallel to axis 855 in the illustrated embodiment) is parallel to a plane in which an anatomical joint encompassed by the external fixation system rotates. The spring hinge 850 is configured such that the axis of rotation 857, as the spring hinge bends in the plane in which the first transverse axis 855 and longitudinal axis 853 are disposed, translates dynamically in conjunction with translation of an anatomical axis of rotation of the treated joint.

Figures 29, 30:
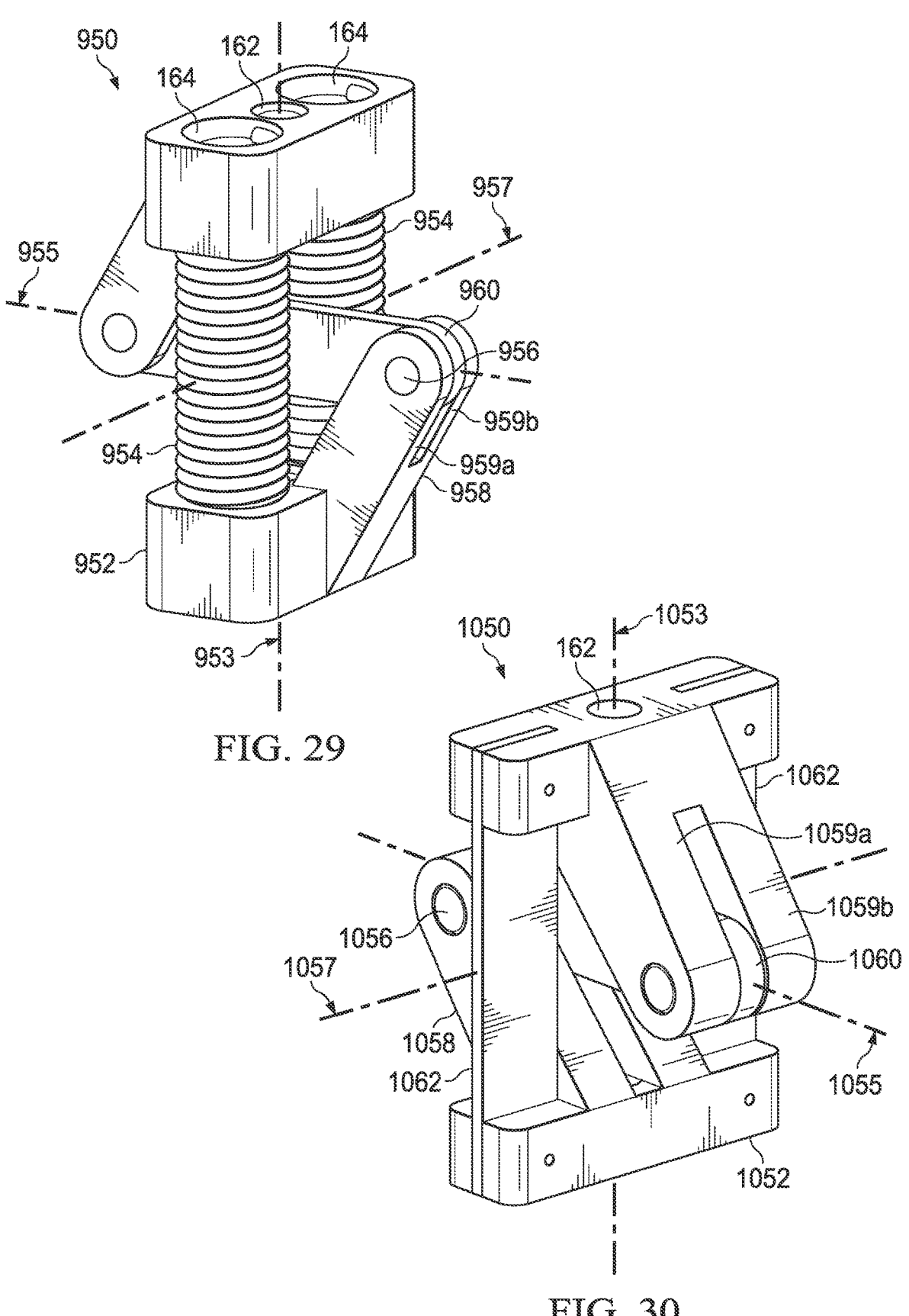
FIG. 29 is a perspective view of double spring hinge with a central link in accordance with the present disclosure.
FIG. 30 is a perspective view of double spring hinge with a central link in accordance with the present disclosure.

FIG. 29 is a perspective view of double spring hinge with a central link in accordance with the present disclosure. This embodiment of a spring hinge may be advantageous for use in external fixation systems about an ankle, knee, or other anatomical joint. Coil springs 954 each extend parallel to a longitudinal axis 953 between two base members 952. Each base member 952 includes an arm 958 extending generally toward the other base member. That is, the arm 958 of the lower base member 952 extends generally upward and the arm 958 of the upper base member 952 extends generally downward. A hinge connector 960 extends between the arms 958 and is secured thereto with a pin joint 956. In this regard, the first base member is secured to the second base member with the hinge connector 960. The hinge connector is disposed internally between two branches 959*a*, 959*b* of each respective arm 958 and passes between the pair of coil springs 954.

The hinge connector 960 and associated pin joints 956 prevent rotation of the spring hinge 950 (e.g., between the two base members) about the longitudinal axis 953 and first transverse axis 955 but facilitate rotation of the spring hinge 950 about the second transverse axis 957. The hinge connector 960 also prevents translation in planes parallel to the transverse axes. The first and second base members 952 are configured to be secured to an external fixation system such that a longitudinal axis of the hinge connector (parallel to axis 955 in the illustrated embodiment) is parallel to a plane in which an anatomical joint encompassed by the external fixation system rotates. The spring hinge 950 is configured such that the axis of rotation 957, as the spring hinge bends in the plane in which the first transverse axis 955 and longitudinal axis 953 are disposed, translates dynamically in conjunction with translation of an anatomical axis of rotation of the treated joint.

FIG. 30 is a perspective view of double spring hinge 1050 with a central link in accordance with the present disclosure, which is similar to the spring hinge 950 and uses flexible blades (similar to those of FIGS. 21-22) instead of coil springs. Flexible blades 1062 each extend parallel to a longitudinal axis 1053 between two base members 1052. Each base member 1052 includes an arm 1058 extending generally toward the other base member. That is, the arm 1058 of the lower base member 1052 extends generally upward and the arm 1058 of the upper base member 1052 extends generally downward. A hinge connector 1060 extends between the arms 1058 and is secured thereto with a pin joint 1056. In this regard, the first base member is secured to the second base member with the hinge connector 1060. The hinge connector is disposed internally between two branches 1059*a*, 1059*b* of each respective arm 1058 and passes between the pair of flexible blades 1062.

The hinge connector 1060 and associated pin joints 1056 prevent rotation of the spring hinge 1050 (e.g., between the two base members) about the longitudinal axis 1053 and first transverse axis 1055 but facilitate rotation of the spring hinge 1050 about the second transverse axis 1057. The hinge connector 1060 also prevents translation in planes parallel to the transverse axes. The first and second base members 1052 are configured to be secured to an external fixation system such that a longitudinal axis of the hinge connector (parallel to axis 1055 in the illustrated embodiment) is parallel to a plane in which an anatomical joint encompassed by the external fixation system rotates. The spring hinge 1050 is configured such that the axis of rotation 1057, as the spring hinge bends in the plane in which the first transverse axis 1055 and longitudinal axis 1053 are disposed, translates dynamically in conjunction with translation of an anatomical axis of rotation of the treated joint.

Figure 31A:
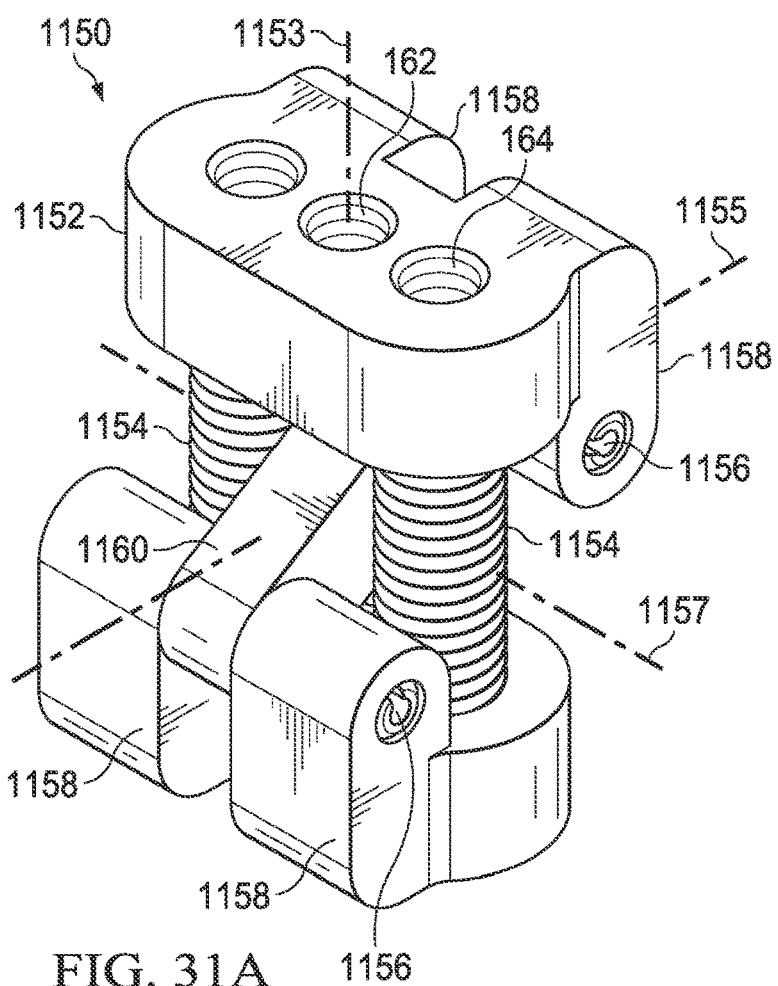
FIGS. 31A and 31B illustrate perspective views of a double spring hinge with a central link in an unexpanded and a flexed configuration, respectively, in accordance with the present disclosure.
Figure 31B:
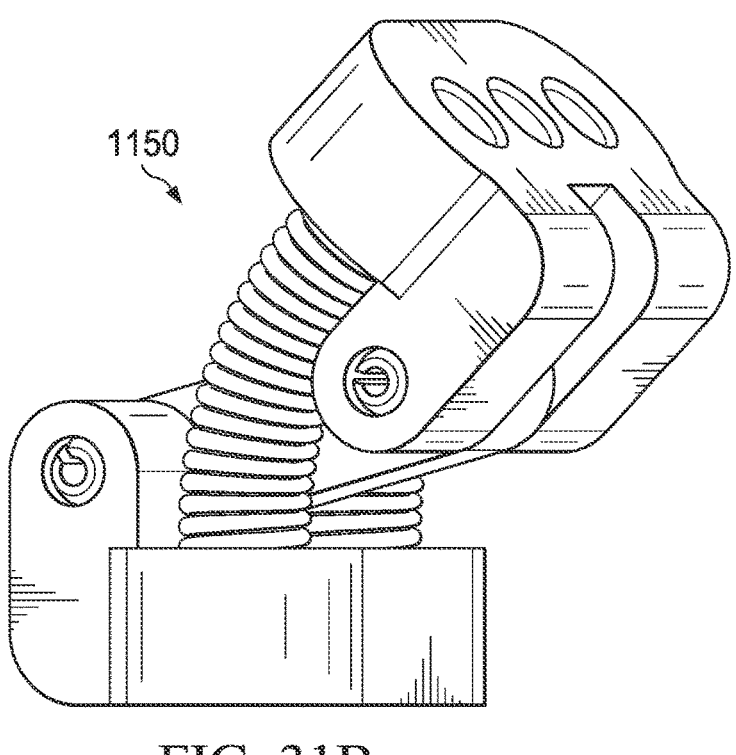

FIGS. 31A and 31B illustrate perspective views of a double spring hinge 1150 with a central link in an unexpanded and a flexed configuration, respectively, in accordance with the present disclosure. Coil springs 1154 each extend parallel to a longitudinal axis 1153 between two base members 1152. Each base member 1152 includes two arms 1158 extending generally toward the other base member. That is, the arms 1158 of the lower base member 1152 extend generally upward and the arms 1158 of the upper base member 1152 extend generally downward. A hinge connector 1160 extends from first and third arms of the first base member to second and fourth arms of the second base member and is secured with pin joints 1156. In this regard, the first base member is secured to the second base member with the hinge connector 1160. The hinge connector is disposed internally between the respective arms 1158 of each base member and passes between the pair of coil springs 1154.

The hinge connector 1160 and associated pin joints 1156 prevent rotation of the spring hinge 1150 (e.g., between the two base members) about the longitudinal axis 1153 and first transverse axis 1155 but facilitate rotation of the spring hinge 1150 about the second transverse axis 1157. The hinge connector 1160 also prevents translation in planes parallel to the transverse axes. The first and second base members 1152 are configured to be secured to an external fixation system such that a longitudinal axis of the hinge connector (extending between the pin joints) is parallel to a plane in which an anatomical joint encompassed by the external fixation system rotates. The spring hinge 1150 is configured such that the axis of rotation 1157, as the spring hinge bends in the plane in which the first transverse axis 1155 and longitudinal axis 1153 are disposed, translates dynamically in conjunction with translation of an anatomical axis of rotation of the treated joint FIG. 32 is an exploded view of the spring hinge of FIGS. 31A and 31B.

Figure 32:
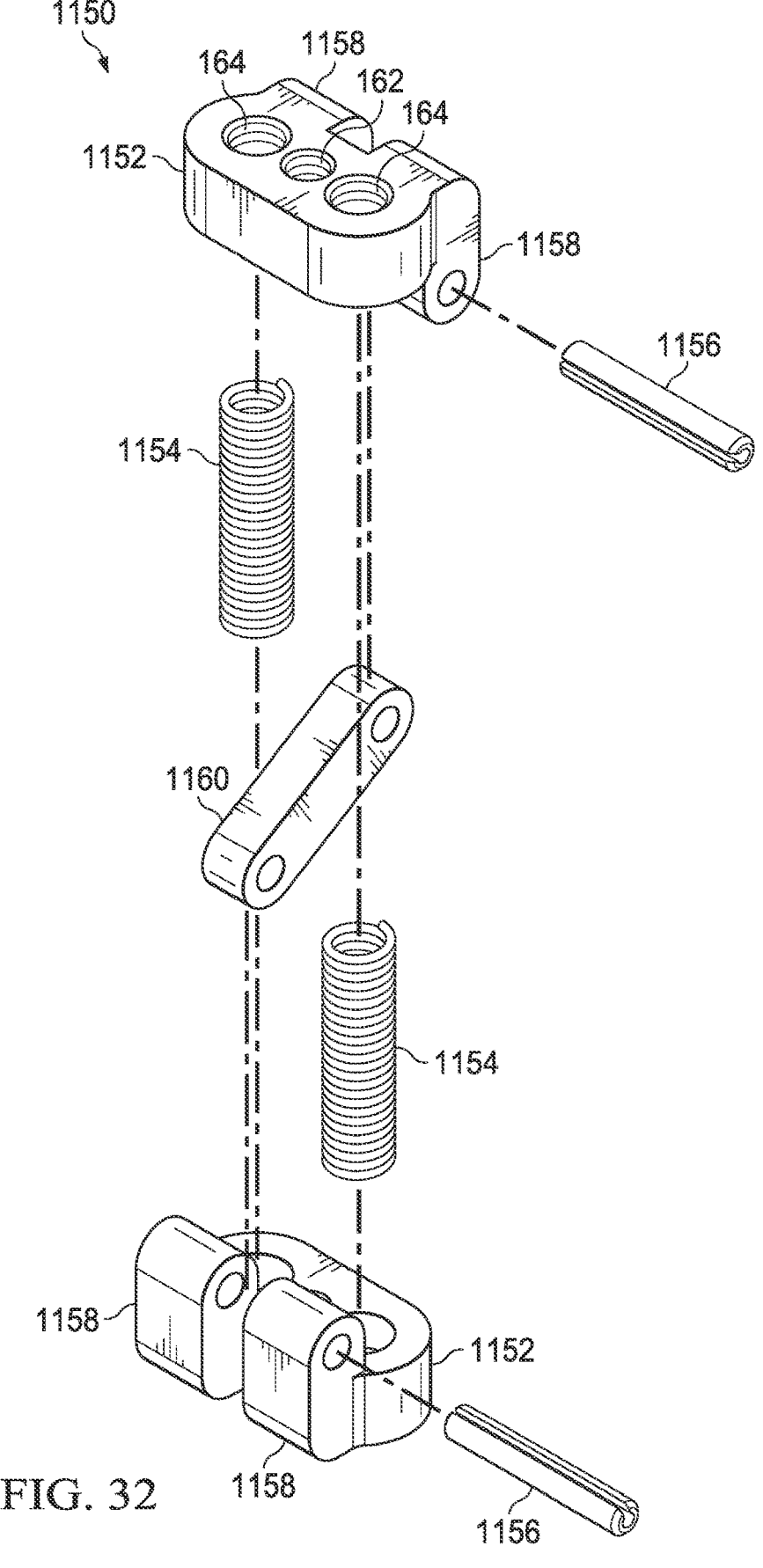
FIG. 32 is an exploded view of the spring hinge of FIGS. 31A and 31B.
Figure 33A:
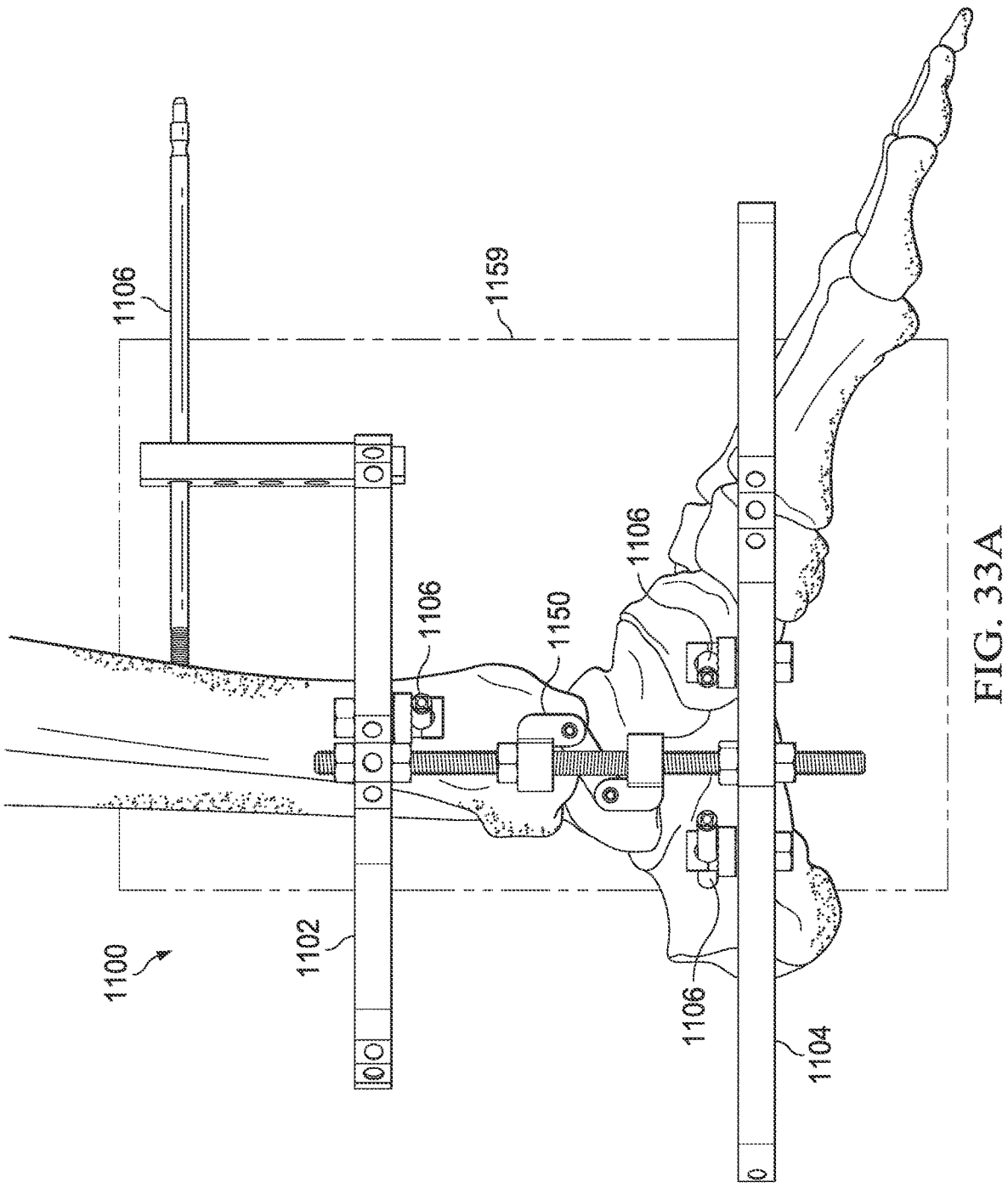
FIG. 33A is a side view of an external fixation system including the spring hinge of FIG. 32 in an ankle fixation application.

FIG. 33A is a side view of an external fixation system including the spring hinge of FIGS. 31A-32 in an ankle fixation application. An external fixation system 1100 includes at least two external fixators, including external fixation ring 1102 and external fixator 1104. A plurality of pins 1106 extend from the external fixators into respective bones around the ankle. A first spring hinge 1150 is disposed between the external fixators to facilitate rotation of the ankle joint within the plane 1159 while preventing other undesirable movement of the ankle. A second spring hinge 1150 (not shown) may be disposed on an opposing side of the external fixation system 1100.

As the foot of the patient is rotated downward or upward about the ankle, the anatomical axis of the ankle will translate. The spring hinges 1150 may similarly permit the first and second external fixators 1102, 1104 to rotate with a translating axis of rotation.

Figure 33B:
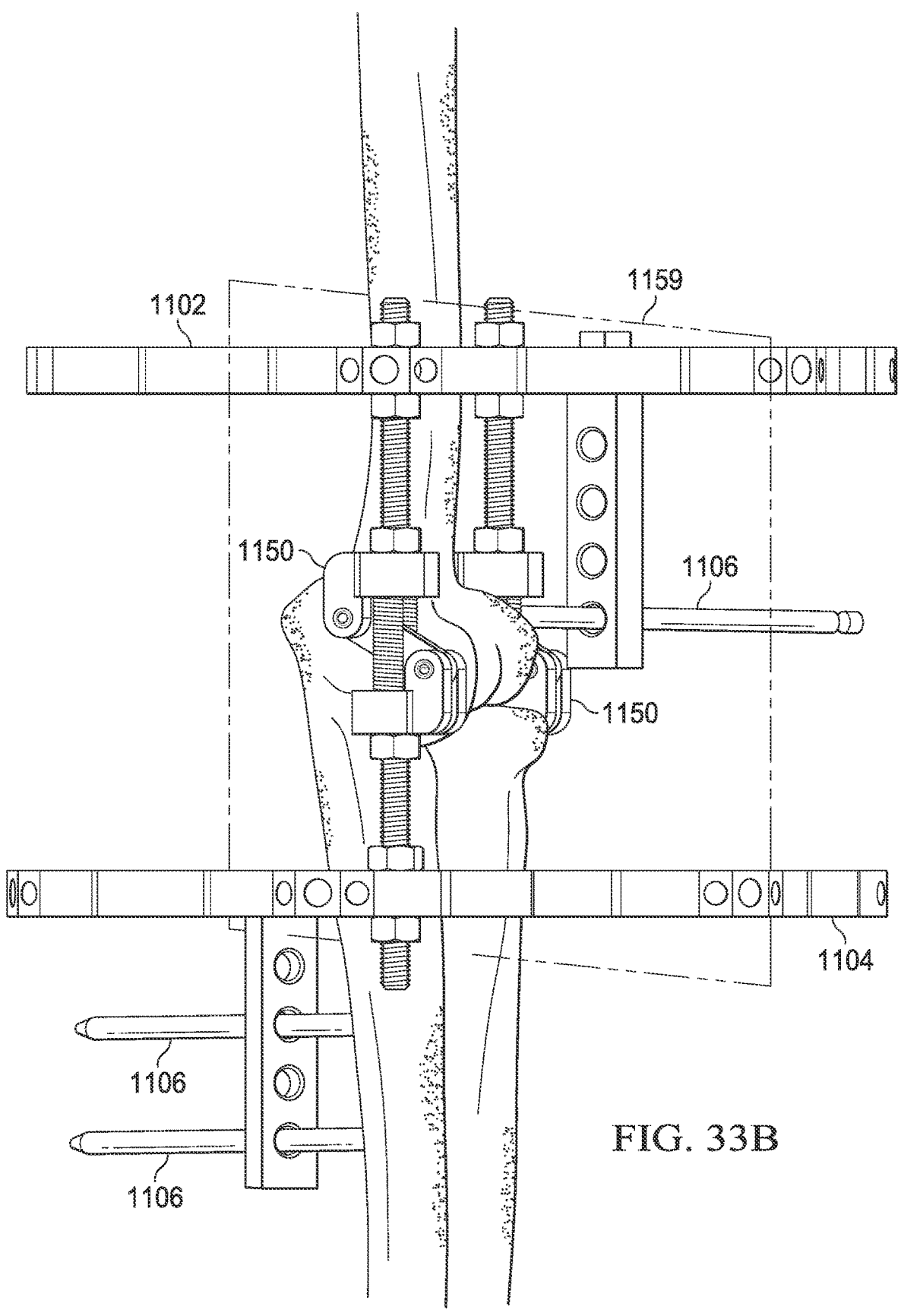
FIG. 33B is a side view of an external fixation system including the spring hinge of FIG. 32 in an elbow fixation application.

FIG. 33B is a side view of an external fixation system including the spring hinge of FIG. 32 in an elbow fixation application. An external fixation system 1100 includes at least two external fixators, including external fixator 1102 and external fixator 1104. A plurality of pins 1106 extend from the external fixators into respective bones (e.g., ulna, radius, and humerus) around the elbow. Spring hinges 1150 are disposed between the external fixators to facilitate rotation of the elbow joint within the plane 1159 while preventing other undesirable movement of the elbow.

Figure 33C:
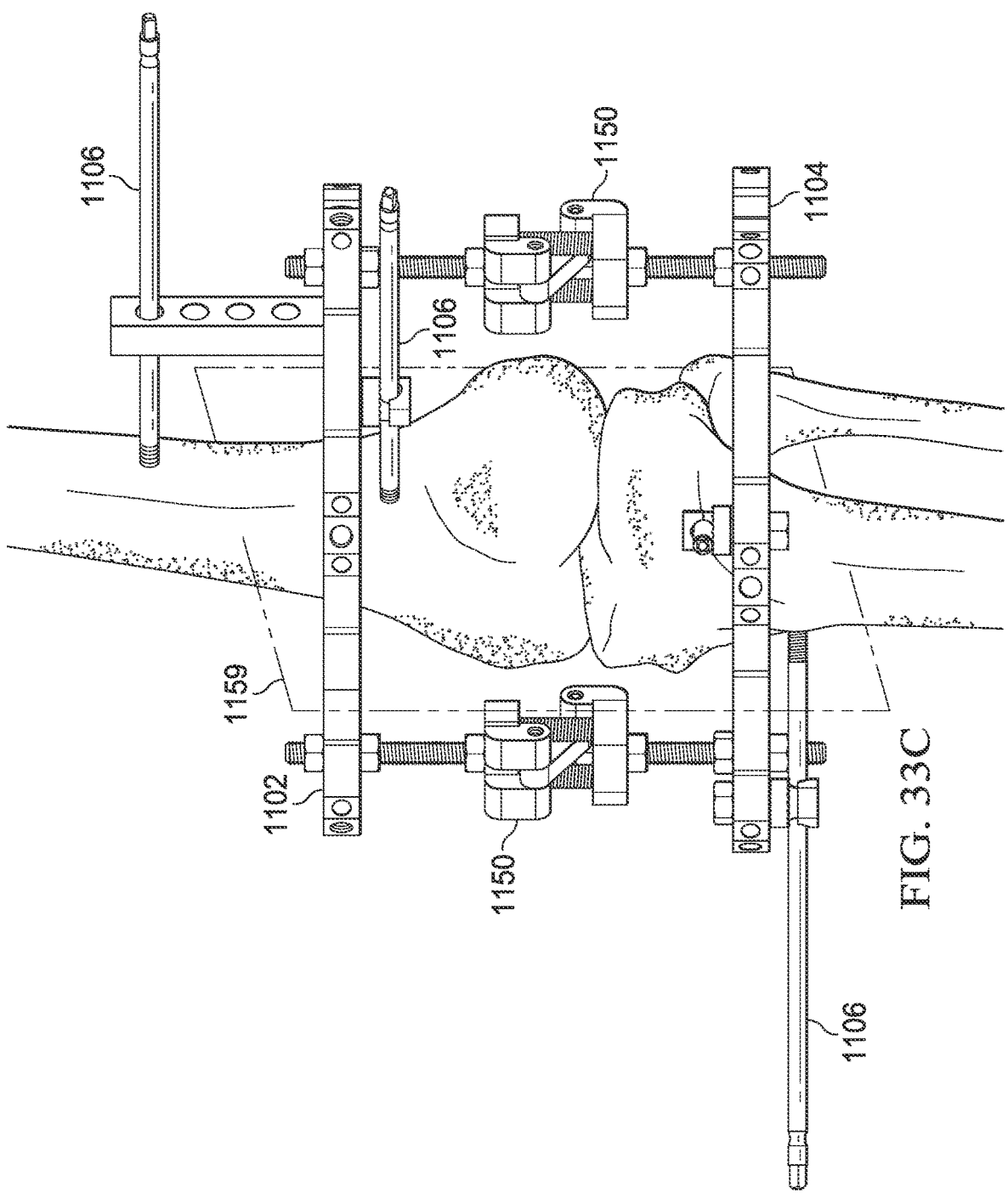
FIG. 33C is a side view of an external fixation system including the spring hinge of FIG. 32 in a knee fixation application.

FIG. 33C is a side view of an external fixation system including the spring hinge of FIG. 32 in a knee fixation application. An external fixation system 1100 includes at least two external fixators, including external fixator 1102 and external fixator 1104. A plurality of pins 1106 extend from the external fixators into respective bones (e.g., femur, fibula, and tibia) around the knee. Spring hinges 1150 are disposed between the external fixators to facilitate rotation of the knee joint within the plane 1159 while preventing other undesirable movement of the knee.

As will be understood by those skilled in the art who have the benefit of the instant disclosure, other equivalent or alternative devices, methods, and systems for orthopedic hinges can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of spring hinges may be varied. In some embodiments, the size of a device and/or system may be scaled up (e.g., to be used for adult subjects) or down (e.g., to be used for juvenile subjects) to suit the needs and/or desires of a practitioner. Where the verb "may" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed devices, systems, and/or methods may exclude any other features or steps beyond those disclosed herein.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting of" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An orthopedic spring hinge connectable between external fixators, comprising:
   a first base member comprising a first arm;
   a second base member comprising a second arm;
   a flexible spring having a longitudinal axis extending from the first base member to the second base member, wherein the first arm is offset from the longitudinal axis of the spring in a first lateral direction from the longitudinal axis and the second arm is offset from the longitudinal axis of the spring in a second lateral direction from the longitudinal axis opposite the first lateral direction; and
   a hinge connector extending from the first arm to the second arm, wherein the hinge connector is configured to pivot with respect to the first arm and the second arm.

2. The orthopedic spring hinge of claim 1, wherein the hinge connector is secured to the first arm with a first pin joint and is secured to the second arm with a second pin joint.

3. The orthopedic spring hinge of claim 1, wherein the spring hinge is configured to prevent rotation of the first base member with respect to the second base member about an axis parallel to the longitudinal axis of the flexible spring.

4. The orthopedic spring hinge of claim 3, wherein the spring hinge is configured to prevent rotation of the first base member with respect to the second base member about a first axis transverse to the longitudinal axis of the flexible spring while permitting rotation of the first base member with respect to the second base member about a second axis transverse to the longitudinal axis of the flexible spring and the first axis.

5. The orthopedic spring hinge of claim 1, wherein each of the first and second base members comprises a bolt connection bore configured to receive a bolt to secure the first and second base members to an external fixation system.

6. The orthopedic spring hinge of claim 1, wherein each of the first and second base members comprises a spring connection bore configured to receive an end of the flexible spring.

7. The orthopedic spring hinge of claim 6, wherein the spring connection bore is internally threaded to engage an external surface of the flexible spring.

8. The orthopedic spring hinge of claim 7, further comprising:

a first dowel, the first dowel being externally threaded to engage an internal surface of a first end portion of the flexible spring to secure the flexible spring to the first base member; and a second dowel, the second dowel being externally threaded to engage an internal surface of a second end portion of the flexible spring to secure the flexible spring to the second base member.

9. The orthopedic spring hinge of claim 8, wherein the first dowel is tapered to exert a force on the flexible spring which increases as the first dowel is threaded into the first end portion of the flexible spring.

10. The orthopedic spring hinge of claim 1, wherein the first and second base members are configured to be secured to an external fixation system such that a longitudinal axis of the hinge connector is parallel to a plane in which an anatomical joint encompassed by the external fixation system rotates.

11. The orthopedic spring hinge of claim 10, wherein the spring hinge is configured such that an axis of rotation of the spring hinge as the flexible spring bends translates dynamically in conjunction with translation of an anatomical axis of rotation of the anatomical joint.

12. The orthopedic spring hinge of claim 1, wherein the flexible spring comprises at least one integrated connector configured to threadingly engage the first base member or the second base member.

13. The orthopedic spring hinge of claim 1, wherein the hinge connector is configured to resist shearing movement between the first base member and the second base member.

14. The orthopedic spring hinge of claim 1, further comprising:

a second hinge connector extending from the first arm to the second arm, wherein the second hinge connector is configured to pivot with respect to the first arm and the second arm, and wherein the hinge connector is disposed on a side of the first arm and the second arm opposite the second hinge connector.

15. The orthopedic spring hinge of claim 1, further comprising:

a second hinge connector extending from a third arm of the first base member to a fourth arm of the second base member, wherein the second hinge connector is configured to pivot with respect to the third arm and the fourth arm, and wherein the hinge connector and the second hinge connector are disposed between the first arm and third arm and between the second arm and the fourth arm.

16. The orthopedic spring hinge of claim 1, further comprising:

a second flexible spring having a longitudinal axis extending from the first base member to the second base member, wherein the hinge connector extends between the flexible spring and the second flexible spring.

17. The orthopedic spring hinge of claim 16, further comprising:

a second flexible spring having a longitudinal axis extending from the first base member to the second base member, wherein the hinge connector extends between the flexible spring and the second flexible spring, the first arm and the second arm are each bifurcated into two branches, and the hinge connector is secured between the two branches of the first arm with a first pin and is secured between the two branches of the second arm with a second pin.

18. The orthopedic spring hinge of claim 17, wherein the flexible spring and the second flexible spring each comprise a coil spring.

19. The orthopedic spring hinge of claim 18, wherein the flexible spring and second flexible spring each comprise a coil spring.

20. The orthopedic spring hinge of claim 17, wherein the flexible spring and the second flexible spring each comprise a blade spring.

21. The orthopedic spring hinge of claim 16, wherein the first base member further comprises a third arm, the second base member further comprises a fourth arm, the hinge connector is secured to the first arm and the third arm with a first pin, and the hinge connector is secured to the second arm and the fourth arm with a second pin.

22. A method for treating an anatomical joint dysfunction comprising:

fixing a first and a second portion of a limb on opposite sides of an anatomical joint with a first external fixator and a second external fixator, such that the first and second external fixators are positioned on either side of the anatomical joint;

connecting the first and second external fixators with an orthopedic spring hinge disposed therebetween, wherein the orthopedic spring hinge comprises:

a first base member comprising a first arm;

a second base member comprising a second arm;

a flexible spring having a longitudinal axis extending from the first base member to the second base member, wherein the first arm is offset from the longitudinal axis of the spring in a first lateral direction from the longitudinal axis and the second arm is offset from the longitudinal axis of the spring in a second lateral direction from the longitudinal axis opposite the first lateral direction; and a hinge connector extending from the first arm to the second arm, wherein the hinge connector is configured to pivot with respect to the first arm and the second arm, wherein the spring hinge is aligned relative to the anatomical joint to permit rotation of the anatomical joint within a first plane parallel to a longitudinal axis of the hinge connector and to restrict translation and rotation of the anatomical joint within planes orthogonal to the first plane.

* * * * *